United States Patent
Parce et al.

[11] Patent Number: 6,042,709
[45] Date of Patent: Mar. 28, 2000

[54] MICROFLUIDIC SAMPLING SYSTEM AND METHODS

[75] Inventors: J. Wallace Parce, Palo Alto; Michael R. Knapp, Redwood City, both of Calif.

[73] Assignee: Caliper Technologies Corp., Mountain View, Calif.

[21] Appl. No.: 09/199,225

[22] Filed: Nov. 24, 1998

Related U.S. Application Data

[63] Continuation of application No. 08/883,638, Jun. 26, 1997, Pat. No. 5,958,203, which is a continuation-in-part of application No. 08/760,446, Dec. 6, 1996, Pat. No. 5,880,071, which is a continuation-in-part of application No. 08/671,986, Jun. 28, 1996, Pat. No. 5,779,868.

[51] Int. Cl.[7] .................... G01N 27/26; G01N 27/473
[52] U.S. Cl. ..................... 204/453; 204/450; 204/600; 204/601; 204/604; 422/100; 436/180
[58] Field of Search .................... 204/450, 451, 204/452, 453, 454, 455, 600, 601, 602, 603, 604, 605; 436/174, 179, 180, 181; 422/100

[56] References Cited

U.S. PATENT DOCUMENTS

| | | |
|---|---|---|
| 4,908,112 | 3/1990 | Pace ................................. 204/601 X |
| 4,963,498 | 10/1990 | Hillman et al. . |
| 5,089,099 | 2/1992 | Chien et al. . |

(List continued on next page.)

FOREIGN PATENT DOCUMENTS

| | | |
|---|---|---|
| 107631 | 5/1984 | European Pat. Off. . |
| 4160356 | 6/1992 | Japan . |
| WO9405414 | 3/1994 | WIPO . |
| WO9604547 | 2/1996 | WIPO . |
| WO9629595 | 9/1996 | WIPO . |
| WO9702357 | 1/1997 | WIPO . |

OTHER PUBLICATIONS

Purnendu K. Dasgupta et al, "Electroasmosis: A Reliable Fluid Propulsion System for Flow Injection Analysis" Analytical Chemistry, vol. 66, No. 11 (Jun. 1, 1994) 1792–1798.

Carlo S. Effenhauser et al, "Glass Chips for High–Speed Capillary Electrophoresis Separations with Submicrometer Plate Heights" Analytical Chemistry, vol. 65, No. 19 (Oct. 1, 1993) 2638–2642.

Bao et al., "Ultramicro enzyme assays in a capillary electrophoretic system," *J. Chromatography.* 608:217–224 (1992) No month available.

Dasgupta, P.K. et al., "Electroosmosis: A Reliable Fluid Propulsion System for Flow Injection Analysis," *Anal. Chem.* 66:1792–1798 Jun. (1994).

Effenhauser et al., "Glass Chips for High–Speed Capillary Electrophoresis Separations with Submicrometer Plate Heights," *Anal. Chem.* 65:2637–2642 Oct. (1993).

(List continued on next page.)

*Primary Examiner*—Jill Warden
*Assistant Examiner*—John S. Starsiak, Jr.
*Attorney, Agent, or Firm*—Matthew B. Murphy

[57] ABSTRACT

The present invention provides for techniques for transporting materials using electrokinetic forces through the channels of a microfluidic system. The subject materials are transported in regions of high ionic concentration, next to spacer material regions of high ionic concentration, which are separated by spacer material regions of low ionic concentration. Such arrangements allow the materials to remain localized for the transport transit time to avoid mixing of the materials. Using these techniques, an electropipettor which is compatible with the microfluidic system is created so that materials can be easily introduced into the microfluidic system. The present invention also compensates for electrophoretic bias as materials are transported through the channels of the microfluidic system by splitting a channel into portions with positive and negative surface charges and a third electrode between the two portions, or by diffusion of the electrophoresing materials after transport along a channel.

91 Claims, 10 Drawing Sheets

U.S. PATENT DOCUMENTS

| | | |
|---|---|---|
| 5,116,471 | 5/1992 | Chien et al. |
| 5,126,022 | 6/1992 | Soane et al. |
| 5,140,161 | 8/1992 | Hillman et al. |
| 5,144,139 | 9/1992 | Hillman et al. |
| 5,164,598 | 11/1992 | Hillman et al. |
| 5,188,963 | 2/1993 | Stapleton . |
| 5,192,405 | 3/1993 | Petersen et al. |
| 5,270,183 | 12/1993 | Corbett et al. |
| 5,282,942 | 2/1994 | Herrick et al. |
| 5,302,264 | 4/1994 | Welch et al. |
| 5,304,487 | 4/1994 | Wilding et al. |
| 5,358,612 | 10/1994 | Dasgupta et al. |
| 5,415,747 | 5/1995 | Holloway . |
| 5,486,335 | 1/1996 | Wilding et al. |
| 5,498,392 | 3/1996 | Wilding et al. |
| 5,536,382 | 7/1996 | Sunzeri . |
| 5,560,811 | 10/1996 | Briggs et al. |
| 5,571,410 | 11/1996 | Swedberg et al. |
| 5,593,838 | 1/1997 | Zanzucchi et al. |
| 5,605,662 | 2/1997 | Heller et al. |
| 5,630,925 | 5/1997 | Pentoney, Jr. et al. |
| 5,890,745 | 4/1999 | Kovacs . |

OTHER PUBLICATIONS

Fan et al., "Micromachining of Capillary Electrophoresis Injectors and Separators on Glass Chips and Evaluation of Flow at Capillary Intersections," *Anal. Chem.* 66:177–184 Jan. (1994).

Harmon et al., "Mathematical Treatment of Electrophoretically Mediated Microanalysis," *Anal. Chem.* 65:2655–2662 Oct. (1993).

Harmon et al., "Selectivity in Electrophoretically Mediated Microanalysis by Control of Product Detection Time," *Anal. Chem.* 66:3797–3805 Nov. (1994).

Harrison et al., "Capillary Electrophoresis and Sample Injection Systems Integrated on a Planar Glass Chip," *Anal. Chem.* 64:1926–1932 Sep. (1992).

Harrison et al., "Micromachining a Miniaturized Capillary Electrophoresis–Based Chemical Analysis System on a Chip," *Science* 261:895–897 Aug. (1993).

Holloway et al., "The analysis of amino acids and peptides by isotachophoresis," *Electrophoresis* 2:127–134 Jul. (1981).

Jacobson et al., "Effects of Injection Schemes and Column Geometry on the Performance of Microchip Electrophoresis Devices," *Anal. Chem.* 66:1107–1113 Apr. (1994).

Jacobson et al., "High–Speed Separations on a Microchip," *Anal. Chem.* 66:1114–1118 Apr. (1994).

Jacobson et al., "Open Channel Electrochromatography on a Microchip," *Anal. Chem.* 66:2369–2373 Jul. (1994).

Jacobson et al., "Precolumn Reactions with Electrophoretic Analysis Integrated on a Microchip," *Anal. Chem.* 66:4127–4124 Dec. (1994).

Jacobson et al., "Fused Quartz Substrates for Microchip Electrophoresis," *Anal. Chem.* 67:2059–2063 Jul. (1995).

Jacobson et al., "Microchip electrophoresis with sample stacking," *Electrophoresis* 16:481–486 (1995) No month available.

Kjellin et al., "Isotachophoresis of CSF Proteins in Gel Tubes Especially Gammaglobulins," *J. Neurol.* 221:225–233 Oct. (1979).

Kopwillem et al., "Serum Protein Fractionation by Isotachophoresis Using Amino Acid Spacers," *J. Chromatography* 118:35–46 (1976).

Linhares et al., "Use of an On–Column Fracture in Capillary Zone Electrophoresis for Sample Introduction," *Anal. Chem.* 63:2076–2078 (1991) No month available.

Manz et al., "Miniaturized Total Chemical Analysis Systems: a Novel Concept for Chemical Sensing," *Sensors and Actuators* B1:244–248 (1990).

Manz et al., "Micromachining of monocrystalline silicon and glass for chemical analysis systems," *Trends in Anal. Chem.* 10:144–149 (1991) No month available.

Manz et al., "Planar chips technology for miniaturization and integration of separation techniques into monitoring systems," *J. Chromatography* 593:253–258 (1992) No month available.

Manz et al., "Electroosmotic pumping and electrophoretic separations for miniaturized chemical analysis systems," *J. Micromech. Microeng.* 4:257–265 (1994) No month available.

Ramsey et al., "Microfabricated chemical measurement systems," *Nature Med.* 1:1093–1096 Oct. (1995).

Sandoval et al., "Method for the Accelerated Measurement of Electroosmosis in Chemically Modified Tubes for Capillary Electrophoresis," *Anal. Chem.* 68:2771–2775 Sep. (1996).

Seiler, K. et al., "Planar Glass Chips for Capillary Electrophoresis: Repetitive Sample Injection, Quantitation, and Separation Efficiency," *Anal. Chem.* 65:1481–1488 May (1993).

Seiler, K. et al., "Electroosmotic Pumping and Valveless Control of Fluid Flow Within a Manifold of Capillaries on a Glass Chip," *Anal. Chem.* 66:3485–3491 Oct. (1994).

Svendsen et al., "Separation of Proteins Using Ampholine Carrier Ampholytes as Buffer and Spacer Ions in an Isotachophoresis System," *Science Tools, The KLB Instrument Journal* 17:13–17 (1970).

MICROFLUIDIC SAMPLING SYSTEM AND METHODS

CROSS-REFERENCE TO RELATED APPLICATIONS

This application is a continuation of U.S. patent application Ser. No. 08/883,638 filed Jun. 26, 1997, now U.S. Pat. No. 5,958,203 which is a continuation-in-part of U.S. patent application Ser. No. 08/760,446, filed Dec. 6, 1996, now U.S. Pat. No. 5,880,071 which is a continuation-in-part of U.S. patent application Ser. No. 08/671,986, filed Jun. 28, 1996, now U.S. Pat. No. 5,779,868 all of which are incorporated herein by reference in their entirety for all purposes.

BACKGROUND OF THE INVENTION

There has been a growing interest in the manufacture and use of microfluidic systems for the acquisition of chemical and biochemical information. Techniques commonly associated with the semiconductor electronics industry, such as photolithography, wet chemical etching, etc., are being used in the fabrication of these microfluidic systems. The term, "microfluidic", refers to a system or device having channels and chambers which are generally fabricated at the micron or submicron scale, e.g., having at least one cross-sectional dimension in the range of from about 0.1 $\mu$m to about 500 $\mu$m. Early discussions of the use of planar chip technology for the fabrication of microfluidic systems are provided in Manz et al., *Trends in Anal. Chem.* (1990) 10(5):144–149 and Manz et al., *Avd. in Chromatog.* (1993) 33:1–66, which describe the fabrication of such fluidic devices and particularly microcapillary devices, in silicon and glass substrates.

Applications of microfluidic systems are myriad. For example, International Patent Appln. WO 96/04547, published Feb. 15, 1996, describes the use of microfluidic systems for capillary electrophoresis, liquid chromatography, flow injection analysis, and chemical reaction and synthesis. U.S. patent application Ser. No. 08/671, 987, filed Jun. 28, 1996, now U.S. Pat. No. 5,942,443 and incorporated herein by reference, discloses wide ranging applications of microfluidic systems in rapidly assaying large number of compounds for their effects on chemical, and preferably, biochemical systems. The phrase "biochemical system," generally refers to a chemical interaction which involves molecules of the type generally found within living organisms. Such interactions include the full range of catabolic and anabolic reactions which occur in living systems including enzymatic, binding, signaling and other reactions. Biochemical systems of particular interest include, e.g., receptor-ligand interactions, enzyme-substrate interactions, cellular signaling pathways, transport reactions involving model barrier systems (e.g., cells or membrane fractions) for bioavailability screening, and a variety of other general systems.

Many methods have been described for the transport and direction of fluids, e.g., samples, analytes, buffers and reagents, within these microfluidic systems or devices. One method moves fluids within microfabricated devices by mechanical micropumps and valves within the device. See, Published U.K. Patent Application No. 2 248 891 (Oct. 18, 1990), Published European Patent Application No. 568 902 (May 2, 1992), U.S. Pat. Nos. 5,271,724 (Aug. 21, 1991) and 5,277,556 (Jul. 3, 1991). See also, U.S. Pat. No. 5,171,132 (Dec. 21, 1990) to Miyazaki et al. Another method uses acoustic energy to move fluid samples within devices by the effects of acoustic streaming. See, Published PCT Application No. 94/05414 to Northrup and White. A straightforward method applies external pressure to move fluids within the device. See, e.g., the discussion in U.S. Pat. No. 5,304,487 to Wilding et al.

Still another method uses electric fields to move fluid materials through the channels of the microfluidic system. See, e.g., Published European Patent Application No. 376 611 (Dec. 30, 1988) to Kovacs, Harrison et al., *Anal. Chem.* (1992) 64:1926–1932 and Manz et al. *J. Chromatog.* (1992) 593:253–258, U.S. Pat. No. 5,126,022 to Soane. Electrokinetic forces have the advantages of direct control, fast response and simplicity. However, there are still some disadvantages. For maximum efficiency, it is desirable that the subject materials be transported as closely together as possible. Nonetheless, the materials should be transported without cross-contamination from other transported materials. Further, the materials in one state at one location in a microfluidic system should remain in the same state after being moved to another location in the microfluidic system. These conditions permit the testing, analysis and reaction of the compound materials to be controlled, when and where as desired.

In a microfluidic system in which the materials are moved by electrokinetic forces, the charged molecules and ions in the subject material regions and in the regions separating these subject material regions are subjected to various electric fields to effect fluid flow.

Upon application of these electric fields, however; differently charged species within the subject material will exhibit different electrophoretic mobilities, i.e., positively charged species will move at a different rate than negatively charged species. In the past, the separation of different species within a sample that was subjected to an electric field was not considered a problem, but was, in fact, the desired result, e.g., in capillary electrophoresis. However, where simple fluid transport is desired, these varied mobilities can result in an undesirable alteration or "electrophoretic bias" in the subject material.

Without consideration and measures to avoid cross-contamination, the microfluidic system must either widely separate the subject materials, or, in the worst case, move the materials one at a time through the system. In either case, efficiency of the microfluidic system is markedly reduced. Furthermore, if the state of the transported materials cannot be maintained in transport, then many applications which require the materials to arrive at a location unchanged must be avoided.

The present invention solves or substantially mitigates these problems of electrokinetic transport. With the present invention, microfluidic systems can move materials efficiently and without undesired change in the transported materials. The present invention presents a high throughput microfluidic system having direct, fast and straightforward control over the movement of materials through the channels of the microfluidic system with a wide range of applications, such as in the fields of chemistry, biochemistry, biotechnology, molecular biology and numerous other fields.

SUMMARY OF THE INVENTION

The present invention provides for a microfluidic system which electroosmotically moves subject material along channels in fluid slugs, also termed "subject material regions," from a first point to a second point in the microfluidic system. A first spacer region of high ionic concentration contacts each subject material region on at least one side and second spacer regions of low ionic concentration are arranged with the subject material regions of subject material and first or high ionic concentration spacer regions so that at least one low ionic concentration region is always between the first and second points to ensure that most of the voltage drop and resulting electric field between the two points is across the low ionic concentration region.

The present invention also provides for a electropipettor which is compatible with a microfluidic system which moves subject materials with electroosmotic forces. The electropipettor has a capillary having a channel. An electrode is attached along the outside length of the capillary and terminates in a electrode ring at the end of the capillary. By manipulating the voltages on the electrode and the electrode at a target reservoir to which the channel is fluidly connected when the end of the capillary is placed into a material source, materials are electrokinetically introduced into the channel. A train of subject material regions, high and low ionic concentration buffer or spacer regions can be created in the channel for easy introduction into the microfluidic system.

The present invention further compensates for electrophoretic bias as the subject materials are electrokinetically transported along the channels of a microfluidic system. In one embodiment a channel between two points of the microfluidic system has two portions with sidewalls of opposite surface charges. An electrode is placed between the two portions. With the voltages at the two points substantially equal and the middle electrode between the two portions set differently, electrophoretic forces are in opposite directions in the two portions, while electroosmotic forces are in the same direction. As subject material is transported from one point to the other, electrophoretic bias is compensated for, while electroosmotic forces move the fluid materials through the channel.

In another embodiment a chamber is formed at the intersection of channels of a microfluidic system. The chamber has sidewalls connecting the sidewalls of the intersecting channels. When a subject material region is diverted from one channel into another channel at the intersection, the chamber sidewalls funnel tile subject material region into the second channel. The width of the second channel is such that diffusion mixes any subject material which had been electrophoretically biased in the subject material region as it traveled along the first channel.

In still a further embodiment, the present invention provides a microfluidic system and method of using that system for controllably delivering a fluid stream within a microfluidic device having at least two intersecting channels. The system includes a substrate having the at least two intersecting channels disposed therein. In this aspect, the one of the channels is deeper than the other channel. The system also includes an electroosmotic fluid direction system. The system is particularly useful where the fluid stream comprises at least two fluid regions having different ionic strengths.

The present invention also provides a sampling system using the electropipettor of the invention. The sampling system includes a sample substrate, which has a plurality of different samples immobilized thereon. Also included is a translation system for moving the electropipettor relative to said sample substrate.

The invention as hereinbefore described may be put into a plurality of different uses, which are themselves inventive, for example, as follows:

The use of a substrate having a channel, in transporting at least a first subject material from at least a first location to a second location along the channel, utilizing at least one region of low ionic concentration which is transported along the channel due to an applied voltage.

A use of the aforementioned invention, in which the ionic concentration of the one region is substantially lower than that of the subject material.

A use of the aforementioned invention, wherein a plurality of subject materials are transported, separated by high ionic concentration spacer regions.

The use of a substrate having a channel along which at least a first subject material may be transported, in electrophoretic bias compensation, the channel being divided into a first and a second portion, in which the wall or walls of the channel are oppositely charged, such that electrophoretic bias on the at least first subject material due to transportation in the first portion is substantially compensated for by electrophoretic bias due to transport in the second portion.

A use of the aforementioned invention in which a first electrode is located at a remote end of the first portion, a second electrode is located at the intersection between the portions and a third electrode is located at a remote end of the second portion.

A use of the aforementioned invention, in which the substrate is a microfluidic system.

A use of the aforementioned invention in which the substrate is an electropipettor.

A use of the aforementioned invention, in which the electropipettor has a main channel for transportation of the subject material and at least one further channel fluidly connected to the main channel from which a further material to be transported along the main channel is obtained.

A use of the aforementioned invention, in which the further material is drawn into the main channel as a buffer region between each of a plurality of separate subject materials.

The use of a microfluidic system having at least a first and a second fluid channel which intersect, in optimizing flow conditions, the channels having different depths.

A use of the aforementioned invention in which one channel is between 2 to 10 times deeper than the other channel.

The use of a microfluidic system having a first channel and a second channel intersecting the first channel, in electrophoretic compensation, the intersection between the channels being shaped such that a fluid being transported along the first channel towards the second channel is mixed at the intersection and any electrophoretic bias in the fluid is dissipated.

DETAILED DESCRIPTION OF THE INVENTION

I. General Organization of a Microfluidic System

Figure 1:
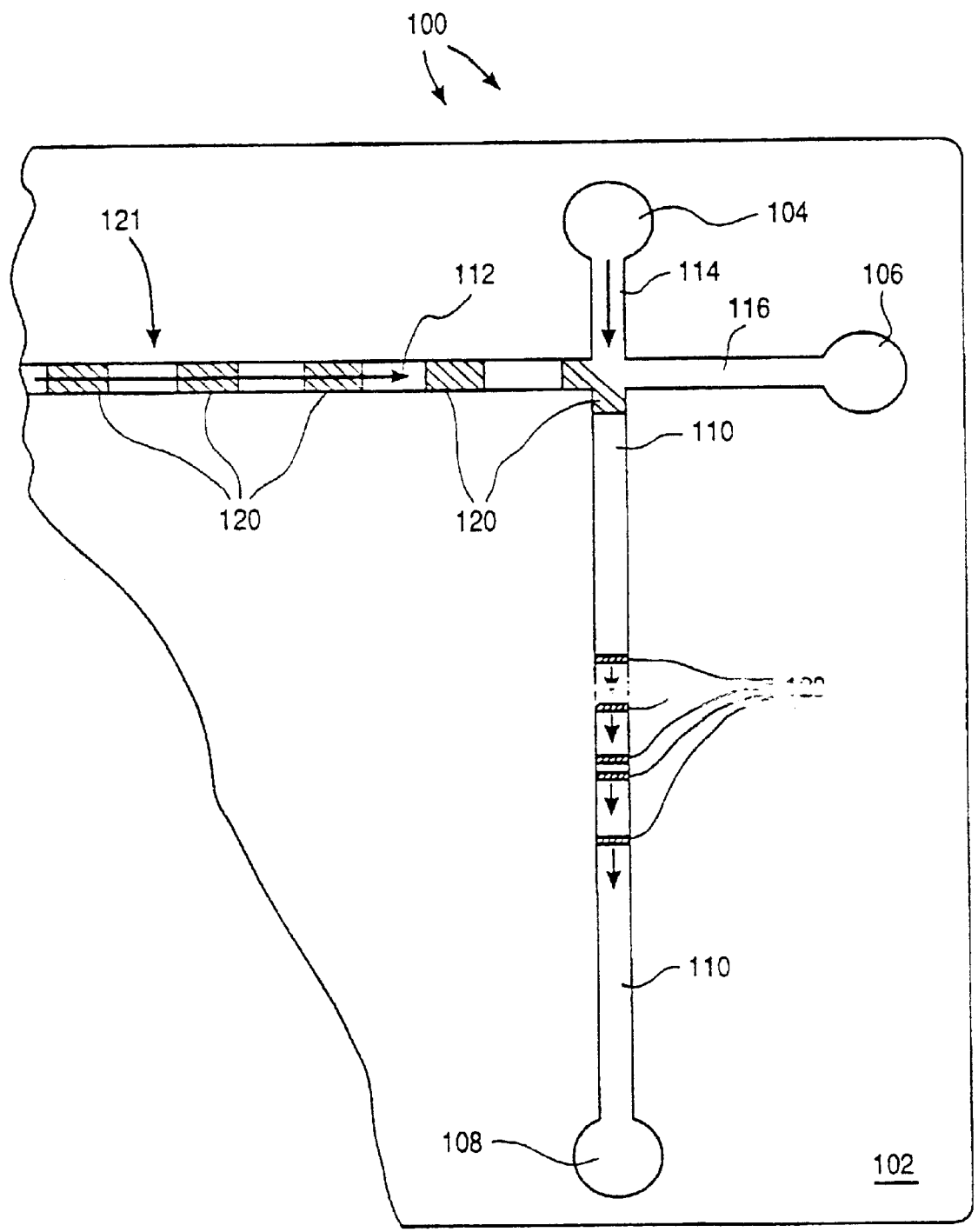
FIG. 1 shows a schematic illustration of one embodiment of a microfluidic system.

FIG. 1 discloses a representative diagram of an exemplary microfluidic system 100 according to the present invention. As shown, the overall device 100 is fabricated in a planar substrate 102. Suitable substrate materials are generally selected based upon their compatibility with the conditions present in the particular operation to be performed by the device. Such conditions can include extremes of pH, temperature, ionic concentration, and application of electrical fields. Additionally, substrate materials are also selected for their inertness to critical components of an analysis or synthesis to be carried out by the system.

Useful substrate materials include, e.g., glass, quartz and silicon, as well as polymeric substrates, e.g., plastics. In the case of conductive or semiconductive substrates, there should be an insulating layer on the substrate. This is particularly important where the device incorporates electrical elements, e.g., electrical fluid direction systems, sensors and the like, or uses electroosmotic forces to move materials about the system, as discussed below. In the case of polymeric substrates, the substrate materials may be rigid, semi-rigid, or non-rigid, opaque, semi-opaque or transparent, depending upon the use for which they are intended. For example, devices which include an optical or visual detection element, will generally be fabricated, at least in part, from transparent materials to allow, or at least, facilitate that detection. Alternatively, transparent windows of, e.g., glass or quartz, may be incorporated into the device for these types of detection elements. Additionally, the polymeric materials may have linear or branched backbones, and may be crosslinked or non-crosslinked. Examples of particularly preferred polymeric materials include, e.g., polydimethylsiloxanes (PDMS), polyurethane, polyvinylchloride (PVC), polystyrene, polysulfone, polycarbonate and the like.

The system shown in FIG. 1 includes a series of channels 110, 112, 114 and 116 fabricated into the surface of the substrate 102. As discussed in the definition of "microfluidic," these channels typically have very small cross sectional dimensions, preferably in the range of from about 0.1 $\mu$m to about 100 $\mu$m. For the particular applications discussed below, channels with depths of about 10 $\mu$m and widths of about 60 $\mu$m work effectively, though deviations from these dimensions are also possible.

Manufacturing of these channels and other microscale elements into the surface of the substrate 102 may be carried out by any number of microfabrication techniques that are well known in the art. For example, lithographic techniques may be employed in fabricating glass, quartz or silicon substrates, for example, with methods well known in the semiconductor manufacturing industries. Photolithographic masking, plasma or wet etching and other semiconductor processing technologies define microscale elements in and on substrate surfaces. Alternatively, micromachining methods, such as laser drilling, micromilling and the like, may be employed. Similarly, for polymeric substrates, well known manufacturing techniques may also be used. These techniques include injection molding techniques or stamp molding methods where large numbers of substrates may be produced using, e.g., rolling stamps to produce large sheets of microscale substrates, or polymer microcasting techniques where the substrate is polymerized within a microfabricated mold.

Besides the substrate 102, the microfluidic system includes an additional planar element (not shown) which overlays the channeled substrate 102 to enclose and fluidly seal the various channels to form conduits. The planar cover element may be attached to the substrate by a variety of means, including, e.g., thermal bonding, adhesives or, in the case of glass, or semi-rigid and non-rigid polymeric substrates, a natural adhesion between the two components. The planar cover element may additionally be provided with access ports and/or reservoirs for introducing the various fluid elements needed for a particular screen.

The system 100 shown in FIG. 1 also includes reservoirs 104, 106 and 108, which are disposed and fluidly connected at the ends of the channels 114, 116 and 110 respectively. As shown, sample channel 112, is used to introduce a plurality of different subject materials into the device. As such, the channel 112 is fluidly connected to a source of large numbers of separate subject materials which are individually introduced into the sample channel 112 and subsequently into another channel 110. As shown, the channel 110 is used for analyzing the subject materials by electrophoresis. It should be noted that the term "subject materials," simply refers to the material, such as a chemical or biological compound, of interest. Subject compounds may include a wide variety of different compounds, including chemical compounds, mixtures of chemical compounds, e.g., polysaccharides, small organic or inorganic molecules, biological macromolecules, e.g., peptides, proteins, nucleic acids, or extracts made from biological materials, such as bacteria, plants, fungi, or animal cells or tissues, naturally occurring or synthetic compositions.

The system 100 moves materials through the channels 110, 112, 114 and 116 by electrokinetic forces which are provided by a voltage controller that is capable of applying selectable voltage levels, simultaneously, to each of the reservoirs, including ground. Such a voltage controller can be implemented using multiple voltage dividers and multiple relays to obtain the selectable voltage levels. Alternatively, multiple independent voltage sources may be used. The voltage controller is electrically connected to each of the reservoirs via an electrode positioned or fabricated within each of the plurality of reservoirs. See, for example, published International Patent Application No. WO 96/04547 to Ramsey, which is incorporated herein by reference in its entirety for all purposes.

II. Electrokinetic Transport

A. Generally

The electrokinetic forces on the fluid materials in the channels of the system 100 may be separated into electroosmotic forces and electrophoretic forces. The fluid control systems used in the system of the present invention employ electroosmotic force to move, direct and mix fluids in the various channels and reaction chambers present on the surface of the substrate 102. In brief, when an appropriate fluid is placed in a channel or other fluid conduit having functional groups present at the surface, those groups can ionize. Where the surface of the channel includes hydroxyl functional groups at the surface, for example, protons can leave the surface of the channel and enter the fluid. Under such conditions, the surface possesses a net negative charge, whereas the fluid possesses an excess of protons or positive charge, particularly localized near the interface between the channel surface and the fluid.

By applying an electric field across the length of the channel, cations flow toward the negative electrode. Movement of the positively charged species in the fluid pulls the solvent with them. The steady state velocity of this fluid movement is generally given by the equation:

$$v = \frac{\epsilon \xi E}{4\pi \eta}$$

where v is the solvent velocity, $\in$ is the dielectric constant of the fluid, $\xi$ is the zeta potential of the surface, E is the electric field strength, and $\eta$ is the solvent viscosity. Thus, as can be easily seen from this equation, the solvent velocity is directly proportional to the zeta potential and the applied field.

Besides electroosmotic forces, there are also electrophoretic forces which affect charged molecules as they move through the channels of the system 100. In the transport of subject materials from one point to another point in the system 100, it is often desirable for the composition of the subject materials to remain unaffected in the transport, i.e., that the subject materials are not electrophoretically differentiated in the transport.

In accordance with the present invention, the subject materials are moved about the channels as slugs of fluid (hereafter termed "subject material regions"), which have a high ionic concentration to minimize electrophoretic forces on the subject materials within these particular regions. To minimize the effect of electrophoretic forces within the subject material regions, regions of spacer fluids ("first spacer regions") are placed on either side of a slug. These first spacer regions have a high ionic concentration to minimize the electric fields in these regions, as explained below, so that subject materials are essentially unaffected by the transport from one location to another location in a microfluidic system. The subject materials are transported through the representative channels 110, 112, 114, 116 of the system 100 in regions of certain ionic strengths, together with other regions of ionic strengths varying from those regions bearing the subject materials.

Figure 2A:
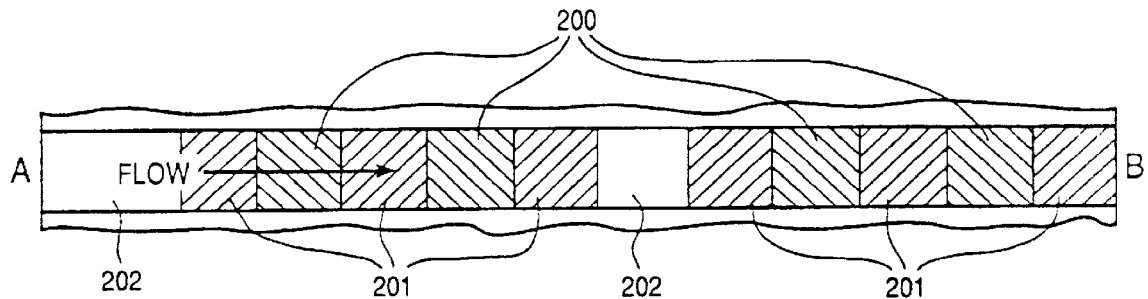
FIG. 2A illustrates an arrangement of fluid regions traveling in a channel of the microfluidic system of FIG. 1, according to one embodiment of the present invention.

A specific arrangement is illustrated in FIG. 2A, which illustrates subject material regions 200 being transported from point A to point B along a channel of the microfluidic system 100. In either side of the subject material regions 200 are first spacer regions 201 of high ionic strength fluid. Additionally, second spacer regions 202 of low ionic concentration fluid periodically separate arrangements of subject material regions 200 and first spacer regions 201. Being of low ionic concentration, most of the voltage drop between points A and B occurs across these second spacer regions 202. The second or low concentration spacer regions 202 are interspersed between the arrangements of subject material region 200 and first spacer region 201 such that, as the subject material regions 200 and the first spacer regions 201 are electroosmotically pumped through the channel, there is always at least one second or low ionic concentration spacer region 202 between the points A and B. This ensures that most of the voltage drop occurs in the second spacer region 202, rather than across the subject material region 200 and first spacer regions 201. Stated differently, the electric field between points A and B is concentrated in the second spacer region 202 and the subject material regions 200 and first spacer regions 201 experience low electric fields (and low electrophoretic forces). Thus, depending upon the relative ionic concentrations in the subject material regions 200, first spacer regions 201 and second or low ionic concentration spacer regions 202, other arrangements of these subject material regions 200, and first and second spacer regions 201 and 202 can be made.

Figure 2B:
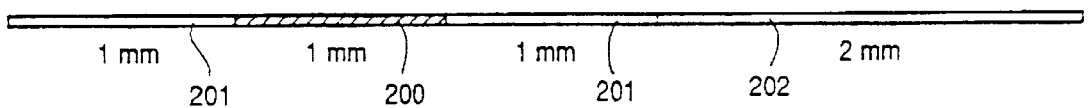
FIG. 2B is a scaled drawing of another arrangement of different fluid regions traveling in a channel of the microfluidic system according to the present invention.

For example, FIG. 2B illustrates an arrangement in which a second or low ionic concentration spacer region 202 is regularly spaced between each combination of first spacer region 201/subject material region 200/first spacer region 201. Such an arrangement ensures that there is always at least one second or low concentration spacer region 202 between points A and B. Furthermore, the drawings are drawn to scale to illustrate the relative lengths of a possible combination of subject material region 200, first or high concentration spacer region 201 and second or low concentration spacer region 202. In the example of FIG. 2B, the subject material region 200 holds the subject material in a high ionic concentration of 150 mM of NaCl. The subject material region 200 is 1 mm long in the channel. The two first spacer regions 201 have ionic concentrations of 150 mM of NaCl. Each first spacer region 201 is 1 mm long. The second spacer region 202 is 2 mm and has an ionic concentration of 5 mM of borate buffer. This particular configuration is designed to maintain a rapidly electrophoresing compound in the subject material region 200 and buffer regions 201 while the compound travels through the channels of the microfluidic system. For example, using these methods, a subject material region containing, e.g., benzoic acid, can be flowed through a microfluidic system for upwards of 72 seconds without suffering excessive electrophoretic bias.

Stated more generally, the velocity of fluid flow, $v_{EoF}$, through the channels of the microfluidic system can be determined and, by measurement, it is possible to determine the total distance, $l_T$, which a subject matter molecule is to travel through the channels. Thus the transit time, $t_{Tr}$, for the subject matter molecule to travel the total distance is:

$$t_{Tr} = l_T/V_{EoF}$$

To contain a subject matter molecule x within the first spacer region 201 next to the subject material region 200, the length of the first spacer region 201, $l^g$, should be greater than the electrophoretic velocity of the subject matter molecule x in the first spacer region 201, $v_{gx}$, multiplied by the transit time:

$$l_g > (v_{gx})(t_{Tr})$$

Since the electrophoretic velocity is proportional to the electric field in the first spacer region 201, the present invention allows control over $v_{gx}$ so that the subject materials can be contained in transport through the microfluidic system channels.

In the arrangements in FIGS. 2A and 2B, the first or high ionic concentration spacer regions 201 help maintain the position of the subject materials in the vicinity of its subject material region 200. No matter what the polarity of the charges of the subject material, the first spacer regions 201 on either side of the subject material region 200 ensures that any subject material leaving the subject material region 200 is only subject to a low electric field due to the relative high ionic concentrations in the first spacer regions 201. If the polarity of the subject material is known, then the direction of the electrophoretic force on the molecules of the subject material is also known.

Figure 3A:
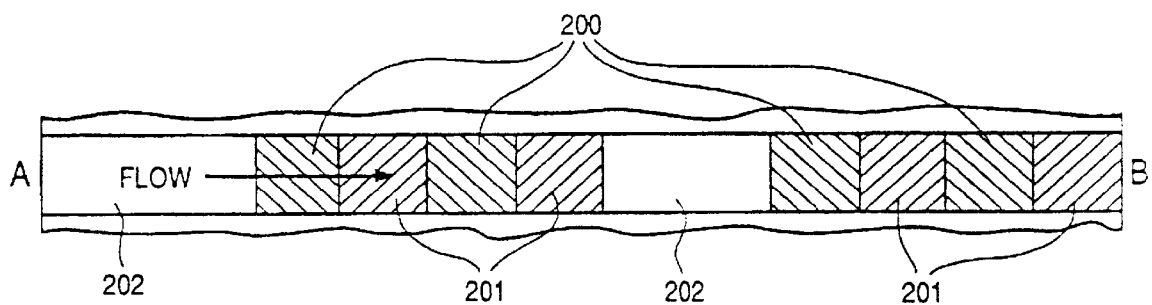
FIG. 3A is another arrangement with high ionic concentration spacer regions before a subject material region traveling within a channel of the microfluidic system.

FIG. 3A illustrates an example where charges of the subject material in all the subject material regions 200 are such that the electrophoretic force on the subject material molecules are in the same direction as the direction of the electroosmotic flow. Hence the first spacer regions 201 precede the subject material regions 200 in the direction of flow. There are no first spacer regions 201 following the subject material regions 200 because the electrophoretic force keeps the subject material from escaping the subject material region 200 in that direction. By eliminating one-half of the first spacer regions 201, more subject material regions 200 with their subject material can be carried per channel length. This enhances the transportation efficiency of the microfluidic system. The second or low ionic concentration spacer regions 202 are arranged with respect to the subject material regions 200 and the first or high ionic concentration spacer regions 201 so that high electric fields fall in the second spacer regions 202 and the electric fields (and electrophoretic forces) in the subject material regions 200 and first spacer regions 201 are kept low.

Figure 3B:
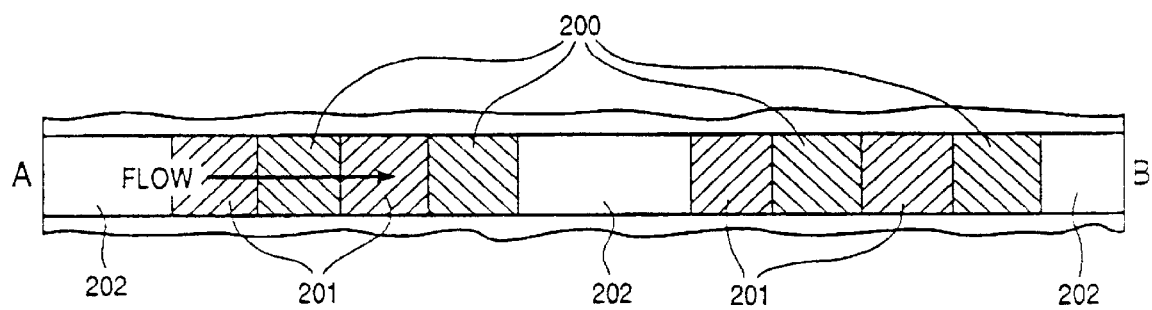
FIG. 3B shows an arrangement with high ionic concentration spacer regions after a subject material region traveling in a channel of the microfluidic system.

In FIG. 3B the first spacer regions 201 follow the subject material regions 200 in the direction of the electroosmotic flow. In this example, the charges of the subject material in all the subject material regions 200 are such that the electrophoretic force on the subject matter molecules are in the opposite direction as the direction of the electroosmotic flow. Hence the subject material may escape the confines of its subject material region, in effect, being left behind by its subject material region 200. The first spacer regions 201 following the subject material regions 200 keep the subject material from migrating too far from its subject material region 200. Likewise, the second or low ionic concentration spacer regions 202 are arranged with the subject material regions 200 and the first or high ionic concentration spacer regions 201 so that high electric fields fall in the second spacer regions 202 and the electric fields in the subject material regions 200 and first spacer regions 201 are kept low.

Various high and low ionic strength solutions are selected to produce a solution having a desired electrical conductivity for the first and second spacer regions 201 and 202. The specific ions that impart electrical conductivity to the solution maybe derived from inorganic salts (such as NaCl, KI, $CaCl_2$, $FeF_3$, $(NH_4)_2SO_4$ and so forth), organic salts (such as pyridinium benzoate, benzalkonium laurate), or mixed inorganic/organic salts (such as sodium benzoate, sodium deoxylsulfate, benzylaminehydrochloride). These ions are also selected to be compatible with the chemical reactions, separations, etc. to be carried out in the microfluidic system. In addition to aqueous solvents, mixtures of aqueous/organic solvents, such as low concentrations of DMSO in water, may be used to assist in the solubilization of the subject matter molecules. Mixtures of organic solvents, such as $CHCl_3$:MeOH, may be also used for the purpose of accelerating assays for phospholipase activity, for example.

Generally, when aqueous solvents are used, solution conductivity is adjusted using inorganic ions. When less polar solvents are used, organic or mixed inorganic/organic ions are typically used. In cases where two immiscible solvents may be simultaneously present (e.g., water and a hydrocarbon such as decane) such that electrical current must flow from one into the other, ionophores (e.g., valinomycin, nonactin, various crown ethers, etc.) and their appropriate ions may be used to conduct current through the non-polar solvent.

B. Electrokinetic Control of Pressure Based Flow

In the electrokinetic flow systems described herein, the presence of differentially mobile fluids (e.g., having a different electrokinetic mobility in the particular system) in a channel may result in multiple different pressures being present along the length of a channel in the system. For example, these electrokinetic flow systems typically employ a series of regions of low and high ionic concentration fluids (e.g., first and second spacer regions and subject material regions of subject material) in a given channel to effect electroosmotic flow, while at the same time, preventing effects of electrophoretic bias within a subject material containing subject material region. As the low ionic concentration regions within the channel tend to drop the most applied voltage across their length, they will tend to push the fluids through a channel. Conversely, high ionic concentration fluid regions within the channel provide relatively little voltage drop across their lengths, and tend to slow down fluid flow due to viscous drag.

As a result of these pushing and dragging effects, pressure variations can generally be produced along the length of a fluid filled channel. The highest pressure is typically found at the front or leading edge of the low ionic concentration regions (e.g., the second spacer regions), while the lowest pressure is typically found at the trailing or back edge of these low ionic strength fluid regions.

While these pressure differentials are largely irrelevant in straight channel systems, their effects can result in reduced control over fluid direction and manipulation in microfluidic devices that employ intersecting channel arrangements, i.e., the systems described in U.S. patent application Ser. No. 08/671,987, now U.S. Pat. No. 5,442,443 previously incorporated by reference. For example, where a second channel is configured to intersect a first channel which contains fluid regions of varying ionic strength, the pressure fluctuations described above can cause fluid to flow in and out of the intersecting second channel as these different fluid regions move past the intersection. This fluctuating flow could potentially, significantly disturb the quantitative electroosmotically driven flow of fluids from the second channel, and/or perturb the various fluid regions within the channel.

By reducing the depth of the intersecting channel, e.g., the second channel, relative to the first or main channel, the fluctuations in fluid flow can be substantially eliminated. In particular, in electroosmotic fluid propulsion or direction, for a given voltage gradient, the rate of flow (volume/time) generally varies as the reciprocal of the depth of the channel for channels having an aspect ratio of >10 (width:depth). With some minor, inconsequential error for the calculation, this general ratio also holds true for lower aspect ratios, e.g., aspect ratios >5. Conversely, the pressure induced flow for the same channel will vary as the third power of the reciprocal of the channel depth. Thus, the pressure build-up in a channel due to the simultaneous presence of fluid regions of differing ionic strength will vary as the square of the reciprocal of the channel depth.

Accordingly, by decreasing the depth of the intersecting second channel relative to the depth of the first or main channel by a factor of X, one can significantly reduce the pressure induced flow, e.g., by a factor of $X^3$, while only slightly reducing the electroosmotically induced flow, e.g., by a factor of X. For example, where the second channel is reduced in depth relative to the first channel by one order of magnitude, the pressure induced flow will be reduced 1000 times while the electroosmotically induced flow will be reduced by only a factor of ten. Accordingly, in some aspects, the present invention provides microfluidic devices as generally described herein, e.g., having at least first and second intersecting channels disposed therein, but where the first channel is deeper than the second channel. Generally, the depths of the channels may be varied to obtain optimal flow conditions for a desired application. As such, depending upon the application, the first channel may be greater than about two time as deep as the second channel, greater than about 5 times as deep as the second channel, and even greater than about ten times as deep as the second channel.

In addition to their use in mitigating pressure effects, varied channel depths may also be used to differentially flow fluids within different channels of the same device, e.g., to mix different proportions of fluids from different sources, and the like.

III. Electropipettor

As described above, any subject material can be transported efficiently through the microfluidic system 100 in or near the subject material regions 200. With the first and second spacer regions 201 and 202, the subject materials are localized as they travel through the channels of the system. For efficient introduction of subject matter into a microfluidic system, the present invention also provides an electropipettor which introduces subject material into a microfluidic system in the same serial stream of combinations of subject material region 200, first and second spacer regions 201 and 202.

A. Structure and Operation

Figure 4A:
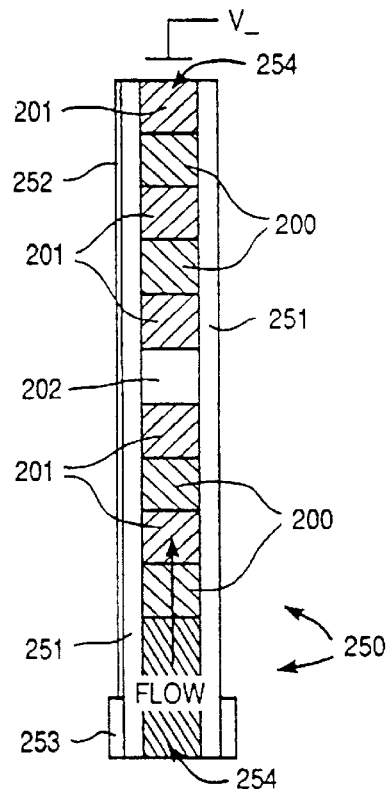
FIG. 4A is a schematic diagram of one embodiment of a electropipettor according to the present invention.

As illustrated in FIG. 4A, an electropipettor 250 is formed by a hollow capillary tube 251. The capillary tube 251 has a channel 254 with the dimensions of the channels of the microfluidic system 100 to which the channel 254 is fluidly connected. As shown in FIG. 4A, the channel 254 is a cylinder having a cross-sectional diameter in the range of 1–100 μm, with a diameter of approximately 30 μm being preferable. An electrode 252 runs down the outside wall of the capillary tube 251 and terminates in a ring electrode 253 around the end of the tube 251. To draw the subject materials in the subject material regions 200 with the buffer regions 201 and 202 into the electropipettor channel 254, the electrode 252 is driven to a voltage with respect to the voltage of a target reservoir (not shown) which is fluidly connected to the channel 254. The target reservoir is in the microfluidic system 100 so that the subject material regions 200 and the buffer regions 201 and 202 already in the channel 254 are transported serially from the electropipettor into the system 100.

Procedurally, the capillary channel end of the electropipettor 250 is placed into a source of subject material. A voltage is applied to the electrode 252 with respect to an electrode in the target reservoir. The ring electrode 253, being placed in contact with the subject material source, electrically biases the source to create a voltage drop between the subject material source and the target reservoir. In effect, the subject material source and the target reservoir become Point A and B in a microfluidic system, i.e., as shown in FIG. 2A. The subject material is electrokinetically introduced into the capillary channel 254 to create a subject material region 200. The voltage on the electrode 252 is then turned off and the capillary channel end is placed into a source of buffer material of high ionic concentration. A voltage is again applied to the electrode 252 with respect to the target reservoir electrode such that the first spacer region 201 is electrokinetically introduced into the capillary channel 254 next to the subject material region 200. If a second or low ionic concentration spacer region 202 is then desirable in the electropipettor channel 254, the end of the capillary channel 254 is inserted into a source of low ionic concentration buffer material and a voltage applied to the electrode 252. The electropipettor 250 can then move to another source of subject material to create another subject material region 200 in the channel 254.

By repeating the steps above, a plurality of subject material regions 200 with different subject materials, which are separated by first and second spacer regions 201 and 202, are electrokinetically introduced into the capillary channel 254 and into the microfluidic system 100.

Note that if the sources of the subject material and the buffer materials (of low and high ionic concentration) have their own electrode, the electrode 252 is not required. Voltages between the target reservoir and the source electrodes operate the electropipettor. Alternatively, the electrode 252 might be in fixed relationship with, but separated from, the capillary tube 251 so that when the end of the tube 251 contacts a reservoir, the electrode 252 also contacts the reservoir. Operation is the same as that described for the FIG. 4A electropipettor.

Figure 4B:
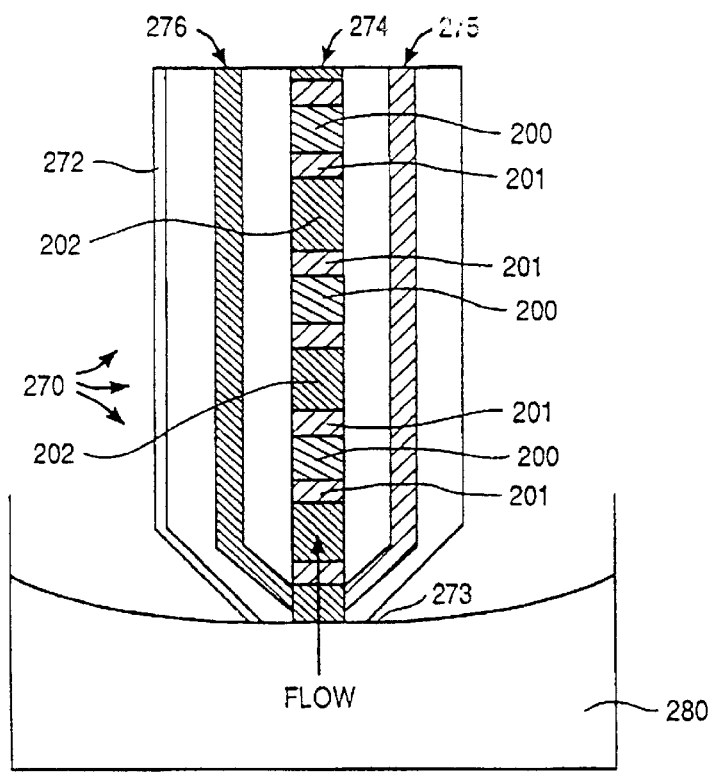
FIG. 4B is a schematic diagram of another electropipettor according to the present invention.
Figure 4C:
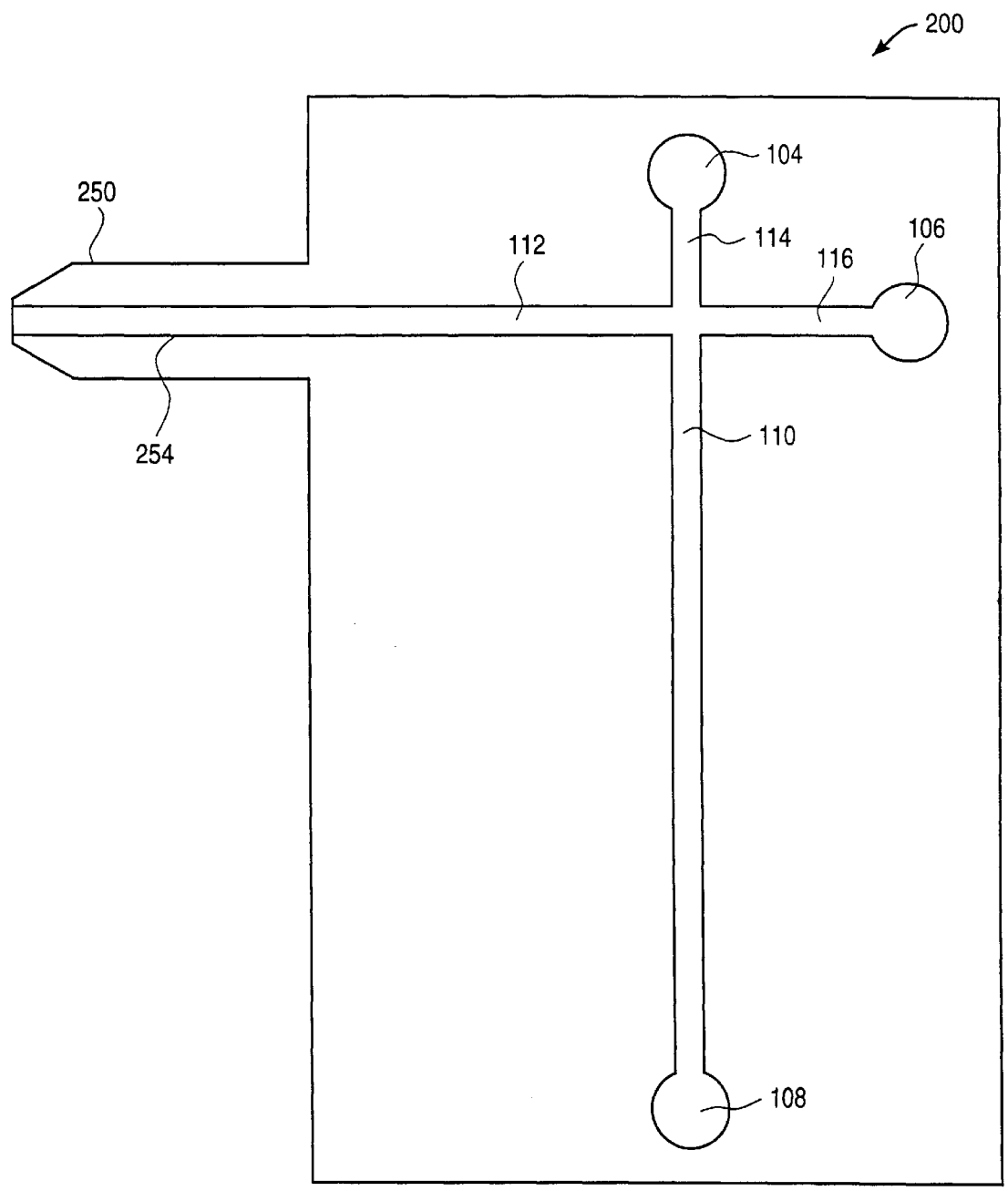
FIG. 4C illustrates the combination of the pipettor with the microfluidic system.
Figure 6D:
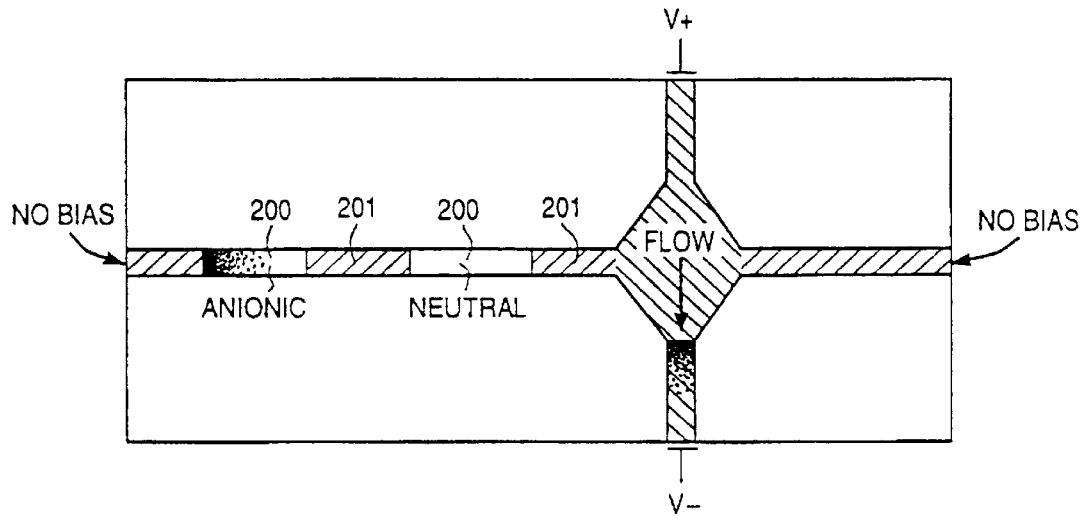
FIGS. 6A–6D illustrate the mixing action of funneling sidewalls at the intersection of channels in a microfluidic system, according to the present invention.

FIG. 4B illustrates a variation of the electropipettor 250 of FIG. 4A. In this variation the electropipettor 270 is not required to travel between a subject material source and buffer material sources to create the first and second spacer regions 201 and 202 within the pipettor. The electropipettor 270 has a body 271 with three capillary channels 274, 275 and 276. The main channel 274 operates identically to the channel 254 of the previously described electropipettor 250. However, the two auxiliary capillary channels 275 and 276 at one end are fluidly connected to buffer source reservoirs (not shown) and the other end of the channels 275 and 276 is fluidly connected to the main channel 274. One reservoir (i.e., connected to auxiliary channel 275) holds buffer material of high ionic concentration, and the other reservoir (i.e., connected to the channel 276) holds buffer material of low ionic concentration.

All of the reservoirs are connected to electrodes for electrically biasing these reservoirs for operation of the electropipettor 270. The electropipettor 270 may also have an electrode 272 along the walls of its body 271 which terminates in a ring electrode 273 at the end of the main channel 274. By applying voltages on the electrode 272 (and ring electrode 273) to create voltage drops along the channels 274, 275, 276, not only can subject material be drawn into the main channel 274 from subject material sources, but buffer material of high and low ionic concentrations can also be drawn from the auxiliary channels 275 and 276 into the main channel 274.

To operate the electropipettor 270 with the electrode 272, the end of the main capillary channel 274 is placed into a source 280 of subject material. A voltage is applied to the electrode 272 with respect to an electrode in the target reservoir to create a voltage drop between the subject material source 280 and the target reservoir. The subject material is electrokinetically drawn into the capillary channel 274. The capillary channel end is then removed from the subject material source 280 and a voltage drop is created between the target reservoir connected to the channel 274 and the reservoir connected to the channel 275. A first or high ionic strength spacer region 201 is formed in the channel 274. Capillary action inhibits the introduction of air into the channel 274 as the buffer material is drawn from the auxiliary channel 275. If a second or low ionic concentration spacer region 202 is then desired in the main channel 274, a voltage is applied to the electrodes in the target reservoir and in the reservoir of low ionic concentration buffer material. A second spacer region 202 is electrokinetically introduced into the capillary channel 274 from the second auxiliary channel 276. The electropipettor 270 can then move to another source of subject material to create another subject material region 200 in the channel 274.

By repeating the steps above, a plurality of subject material regions 200 with different subject materials, which are separated by first and second spacer regions 201 and 202, are electrokinetically introduced into the capillary channel 274 and into the microfluidic system 100.

If it is undesirable to expose the subject material source to oxidation/reduction reactions from the ring electrode 273, the electropipettor may be operated without the electrode 272. Because electroosmotic flow is slower in solutions of higher ionic strength, the application of a potential (− to +) from the reservoir connecting the channel 274 to the reservoir connecting the channel 275 results in the formation of a vacuum at the point where the channels 274 and 275 intersect. This vacuum draws samples from the subject material source into the channel 274. When operated in this mode, the subject material is somewhat diluted with the solutions in the channels 275 and 276. This dilution can be mitigated by reducing the relative dimensions of the channels 276 and 275 with respect to the channel 274.

To introduce first and second spacer regions 201 and 202 into the capillary channel 274, the electropipettor 270 is operated as described above. The capillary channel end is removed from the subject material source 280 and a voltage drop is created between the target reservoir for the channel 274 and the reservoir connected to the selected channels 275 or 276.

Although generally described in terms of having two auxiliary channels and a main channel, it will be appreciated that additional auxiliary channels may also be provided to introduce additional fluids, buffers, diluents, reagents and the like, into the main channel.

As described above for intersecting channels within a microfluidic device, e.g., chip, pressure differentials resulting from differentially mobile fluids within the different pipettor channels also can affect the control of fluid flow within the pipettor channel. Accordingly, as described above, the various pipettor channels may also be provided having varied channel depths relative to each other, in order to optimize fluid control.

B. Method of Electropipettor Manufacture

The electropipettor might be created from a hollow capillary tube, such as described with respect to FIG. 4A. For more complex structures, however, the electropipettor is optimally formed from the same substrate material as that of the microchannel system discussed above. The electropipettor channels (and reservoirs) are formed in the substrate in the same manner as the microchannels for a microfluidic system and the channeled substrate is covered by a planar cover element, also described above. The edges of the substrate and cover element may then be shaped to the proper horizontal dimensions of the pipettor, especially its end, as required. Techniques, such as etching, air abrasion (blasting a surface with particles and forced air), grinding and cutting, may be used. Electrodes are then created on the surface of the substrate and possibly cover, as required. Alternatively, the edges of the substrate and the cover element may be shaped prior to being attached together. This method of manufacture is particularly suited for multichannel electropipettors, such as described immediately above with respect to FIG. 4B and described below with respect to FIG. 8.

IV. Sampling System

As described above, the methods, systems and apparatuses described above will generally find widespread applicability in a variety of disciplines. For example, as noted previously, these methods and systems may be particularly well suited to the task of high throughput chemical screening in, e.g., drug discovery applications, such as is described in copending U.S. patent application Ser. No. 08/671,987, filed Jun. 28, 1996, now U.S. Pat. No 5,942,443 and previously incorporated by reference.

A. Sample Matrices

The pipetting and fluid transport systems of the invention are generally described in terms of sampling numbers of liquid samples, i.e., from multi-well plates. In many instances, however, the number or nature of the liquid based samples to be sampled may generate sample handling problems. For example, in chemical screening or drug discovery applications, libraries of compounds for screening may number in the thousands or even the hundreds of thousands. As a result, such libraries would require extremely large numbers of sample plates, which, even with the aid of robotic systems, would create myriad difficulties in sample storage, manipulation and identification. Further, in some cases, specific sample compounds may degrade, complex or otherwise possess relatively short active half-lives when stored in liquid form. This can potentially result in suspect results where samples are stored in liquid form for long periods prior to screening.

Accordingly, the present invention provides sampling systems which address these further problems, by providing the compounds to be sampled in an immobilized format. By "immobilized format" is meant that the sample material is provided in a fixed position, either by incorporation within a fixed matrix, i.e., porous matrix, charged matrix, hydrophobic or hydrophilic matrix, which maintains the sample in a given location. Alternatively, such immobilized samples include samples spotted and dried upon a given sample matrix. In preferred aspects, the compounds to be screened are provided on a sample matrix in dried form. Typically, such sample matrices will include any of a number of materials that can be used in the spotting or immobilization of materials, including, e.g., membranes, such as cellulose, nitrocellulose, PVDF, nylon, polysulfone and the like. Typically, flexible sample matrices are preferred, to permit folding or rolling of the sample matrices which have large numbers of different sample compounds immobilized thereon, for easy storage and handling.

Generally, samples may be applied to the sample matrix by any of a number of well known methods. For example, sample libraries may be spotted on sheets of a sample matrix using robotic pipetting systems which allow for spotting of large numbers of compounds. Alternatively, the sample matrix may be treated to provide predefined areas for sample localization, e.g., indented wells, or hydrophilic regions surrounded by hydrophobic barriers, or hydrophobic regions surrounded by hydrophilic barriers (e.g., where samples are originally in a hydrophobic solution), where spotted materials will be retained during the drying process. Such treatments then allow the use of more advanced sample application methods, such as those described in U.S. Pat. No. 5,474,796, wherein a piezoelectric pump and nozzle system is used to direct liquid samples to a surface. Generally, however, the methods described in the '796 patent are concerned with the application of liquid samples on a surface for subsequent reaction with additional liquid samples. However, these methods could be readily modified to provide dry spotted samples on a substrate.

Other immobilization or spotting methods may be similarly employed. For example, where samples are stable in liquid form, sample matrices may include a porous layer, gel or other polymer material which retain a liquid sample without allowing excess diffusion, evaporation or the like, but permit withdrawal of at least a portion of the sample material, as desired. In order to draw a sample into the pipettor, the pipettor will free a portion of the sample from the matrix, e.g., by dissolving the matrix, ion exchange, dilution of the sample, and the like.

B. Resolubilizing Pipettor

As noted, the sampling and fluid transport methods and systems of the present invention are readily applicable to screening, assaying or otherwise processing samples immobilized in these sample formats. For example, where sample materials are provided in a dried form on a sample matrix, the electropipetting system may be applied to the surface of the matrix. The electropipettor is then operated to expel a small volume of liquid which solubilizes the previously dried sample on the matrix surface (dissolves a retaining matrix, or elutes a sample from an immobilizing support), e.g., by reversing the polarity of the field applied to the pipettor, or by applying a potential from the low ionic concentration buffer reservoir to the high ionic concentration buffer reservoir, as described above. Once the sample is resolubilized, the pipettor is then operated in its typical forward format to draw the solubilized sample into the pipettor channel as previously described.

Figure 8:
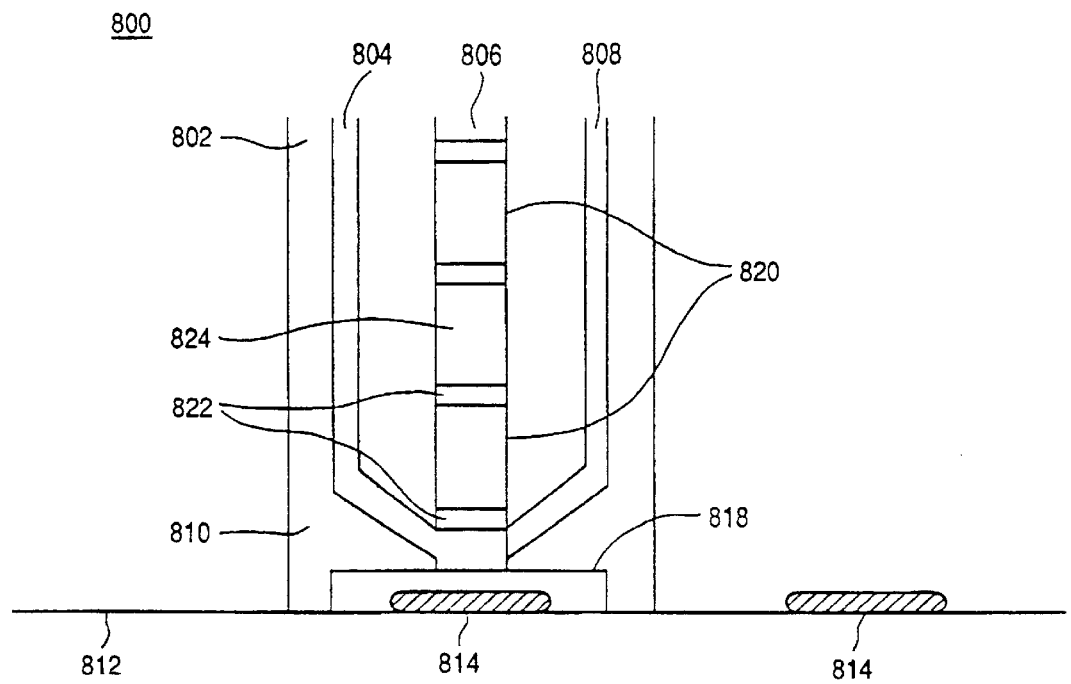
FIG. 8 shows a schematic illustration of an electropipettor for use with a sampling system using samples immobilized, e.g., dried, on a substrate sheet or matrix.

A schematic illustration of one embodiment of an electropipettor useful in performing this function, and its operation, is shown in FIG. 8. Briefly, the top end 802 of the pipettor (as shown) 800 is generally connected to the assay system, e.g., a microfluidic chip, such that voltages can be supplied independently to the three channels of the pipettor 804, 806 and 808. Channels 804 and 808 are typically fluidly connected to buffer reservoirs containing low and high ionic concentration fluids, respectively. In operation, the tip of the pipettor 810 is contacted to the surface of a sample matrix 812 where an immobilized(e.g., dried) sample 814 is located. A voltage is applied from the low ionic concentration buffer channel 804 to the high ionic concentration buffer channel 808, such that buffer is forced out of the end of the pipettor tip to contact and dissolve the sample. As shown, the pipettor tip 816 may include a recessed region or "sample cup" 818 in order to maintain the expelled solution between the pipettor tip and the matrix surface. In some cases, e.g., where organic samples are being screened, in order to ensure dissolution of the sample, an appropriate concentration of an acceptable solvent, e.g., DMSO, may be included with the low ionic concentration buffer. Voltage is then applied from the high ionic concentration buffer channel to the sample channel 806 to draw the sample into the pipettor in the form of a sample plug 820. Once the sample is completely withdrawn from the sample cup into the pipettor, the high surface tension resulting from air entering the sample channel will terminate aspiration of the sample, and high ionic concentration buffer solution will begin flowing into the sample channel to form a first spacer region 822, following the sample. Low ionic concentration buffer solution may then be injected into the sample channel, i.e., as a second spacer region 824, by applying the voltage from the low ionic concentration buffer channel 804 to the sample channel 806. Prior to or during presentation of the next sample position on the matrix, a first or high ionic concentration spacer region 822 may be introduced into the sample channel by applying the voltage between the high ionic concentration buffer channel and the sample channel. As noted previously, a roll, sheet, plate, or numerous rolls, sheets or plates, of sample matrix having thousands or hundreds of thousands of different compounds to be screened, may be presented in this manner, allowing their serial screening in an appropriate apparatus or system.

V. Elimination of Electrophoretic Bias

As explained above, electrokinetic forces are used to transport the subject material through the channels of the microfluidic system 100. If the subject material is charged in solution, then it is subject to not only electroosmotic forces, but also to electrophoretic forces. Thus the subject material is likely to have undergone electrophoresis in traveling from one point to another point along a channel of the microfluidic system. Hence the mixture of the subject material or the localization of differently charged species in a subject material region 200 at the starting point is likely to be different than the mixture or localization at the arrival point. Furthermore, there is the possibility that the subject material might not even be in the subject material region 200 at the arrival point, despite the first spacer regions 201.

Figure 5:
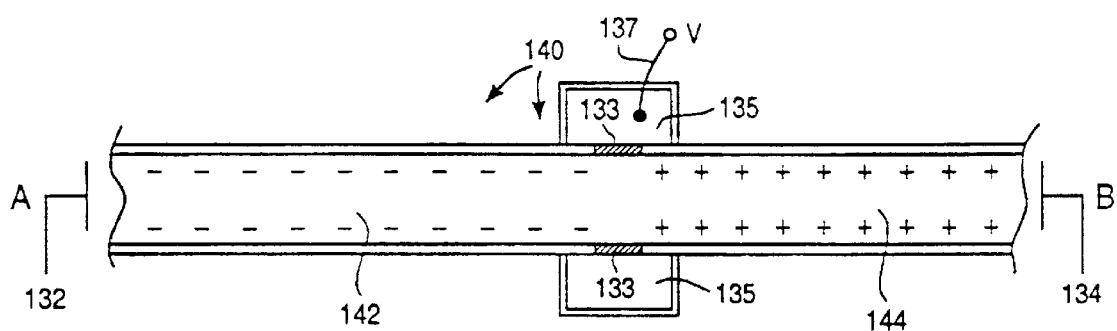
FIG. 5 is a schematic diagram of a channel having portions with oppositely charged sidewalls in a microfluidic system, according to the present invention.

Therefore, another aspect of the present invention compensates for electrophoretic bias as the subject materials are transported through the microfluidic system 100. One way to compensate for electrophoretic bias is illustrated in FIG. 5. In the microfluidic system 100 described above, each of the channels 110, 112, 114 and 116 was considered as a unitary structure along its length. In FIG. 5, an exemplary channel 140 is divided into two portions 142 and 144. The sidewalls of each channel portion 142 and 144 have surface charges which are of opposite polarity. The two channel portions 142 and 144 are physically connected together by a salt bridge 133, such as a glass frit or gel layer. While the salt bridge 133 separates the fluids in the channel 140 from an ionic fluid in a reservoir 135 which is partially defined by the salt bridge 133, the salt bridge 133 permits ions to pass through. Hence the reservoir 135 is in electrical, but not fluid, communication with the channel 140.

To impart electroosmotic and electrophoretic forces along the channel 140 between points A and B, electrodes 132 and 134 are arranged at points A and B respectively.

Additionally, a third electrode 137 is placed in the reservoir 135 at the junction of the two portions 142 and 144. The electrodes 132 and 134 are maintained at the same voltage and the electrode 137 at another voltage. In the example illustrated in FIG. 5, the two electrodes 132 and 134 are at a negative voltage, while the electrode 137 and hence the junction of the two portions 142 and 144 are at zero voltage, i.e., ground. Thus the voltage drops, and hence the electric fields, in the portions 142 and 144 are directed in opposite directions. Specifically, the electric fields point away from each other. Thus the electrophoretic force on a particularly charged molecule is in one direction in the channel portion 142 and in the opposite direction in the channel portion 144. Any electrophoretic bias on a subject material is compensated for after traveling through the two portions 142 and 144.

The electroosmotic force in both portions 142 and 144 are still in the same direction, however. For example, assuming that the sidewalls of the channel portion 142 have positive surface charges, which attract negative ions in solution, and the sidewalls of the channel portion 144 have negative surface charges, which attract positive ions in solution, as shown in FIG. 5, the electroosmotic force in both portions 142 and 144 is to the right of the drawing. Thus the subject material is transported from point A to point B under electroosmotic force, while the electrophoretic force is in one direction in one portion 142 and in the opposite direction in the other portion 144.

To create a channel with sidewalls having positive or negative surface charges, one or both portions of the channel is coated with insulating film materials with surface charges, such as a polymer. For example, in the microfluidic system 100 the substrate 102 and the channels may be formed of glass. A portion of each channel is coated with a polymer of opposite surface charge, such as polylysine, for example, or is chemically modified with a silanizing agent containing an amino function, such as aminopropyltrichlorosilane, for example. Furthermore, the surface charge densities and volumes of both channel portions should be approximately the same to compensate for electrophoretic bias.

Rather than being formed in a solid planar substrate, the channel can also be formed by two capillary tubes which are butted together with a salt bridge which separates an ionic fluid reservoir from fluids in the capillary tubes. An electrode is also placed in the ionic fluid reservoir. One capillary tube has a negative surface charge and the other capillary tube a positive surface charge. The resulting capillary channel operates as described above.

FIGS. 6A–6D illustrates another embodiment of the present invention for which the effects of electrophoretic bias induced upon the subject material is moving from point A to point B are compensated. In this embodiment the subject material is mixed at point B, an intersection between two channels, such as illustrated in FIG. 1.

FIGS. 6A–6D show a chamber 160 is formed at the intersection of the channels 150, 152, 154 and 156. The chamber 160 has four sidewalls 162, 164, 166 and 168. The sidewall 162 connects a sidewall of the channel 152 to a sidewall of the channel 150; the sidewall 164 connects a sidewall of the channel 154 to the other sidewall of the channel 152; the sidewall 166 connects a sidewall of the channel 156 to the other sidewall of the channel 154; and the sidewall 168 connects the opposite sidewall of the channel 156 to the opposite sidewall of the channel 150. Assuming a flow of materials through the channel 152 toward the channel 156, the sidewalls 162 and 168 form as a funnel if the materials are diverted into the channel 150.

The dimensions of the sidewalls 162 and 168 accommodate the length of a subject material plug 200 traveling along the channel 152. The sidewalls 162 and 168 funnel down the plug 200 into the width of the channel 150. The width of the channel 150 is such that diffusion of the subject material occurs across the width of the channel 150, i.e., mixing occurs and any electrophoretic bias of the subject material created in the subject material region 200 traveling along the channel 162 is eliminated. For example, if the channel 150 is 50 $\mu$m wide, diffusion across the channel occurs in approximately one second for a molecule having a diffusion constant of $1 \times 10^{-5}$ cm$^2$/sec.

Figure 6A:
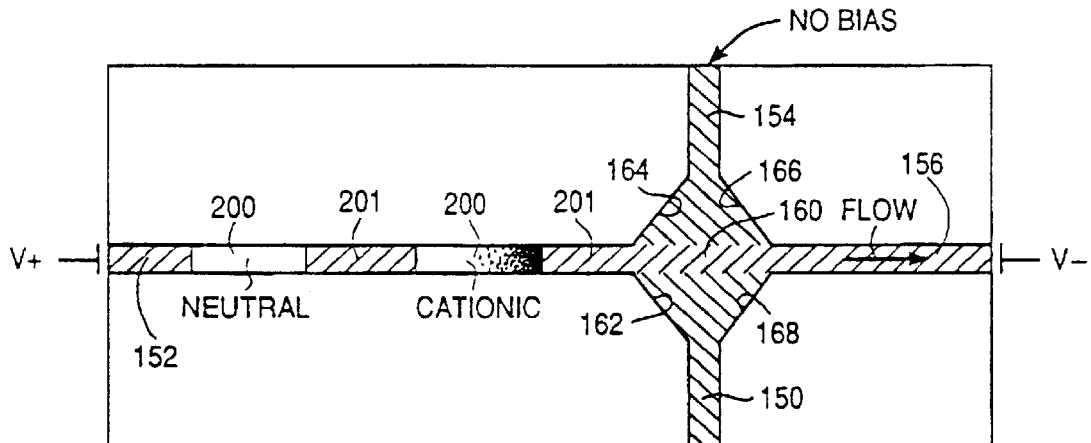
Figure 6B:
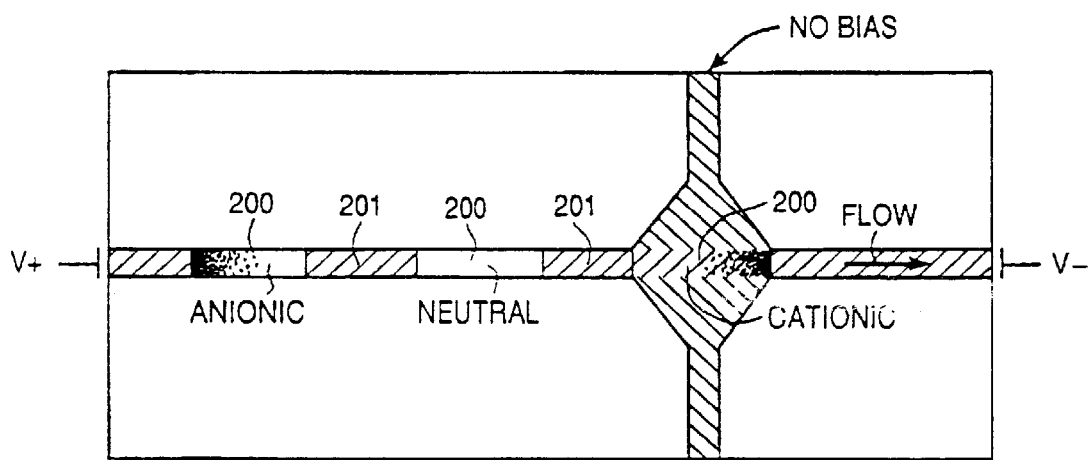
Figure 6C:
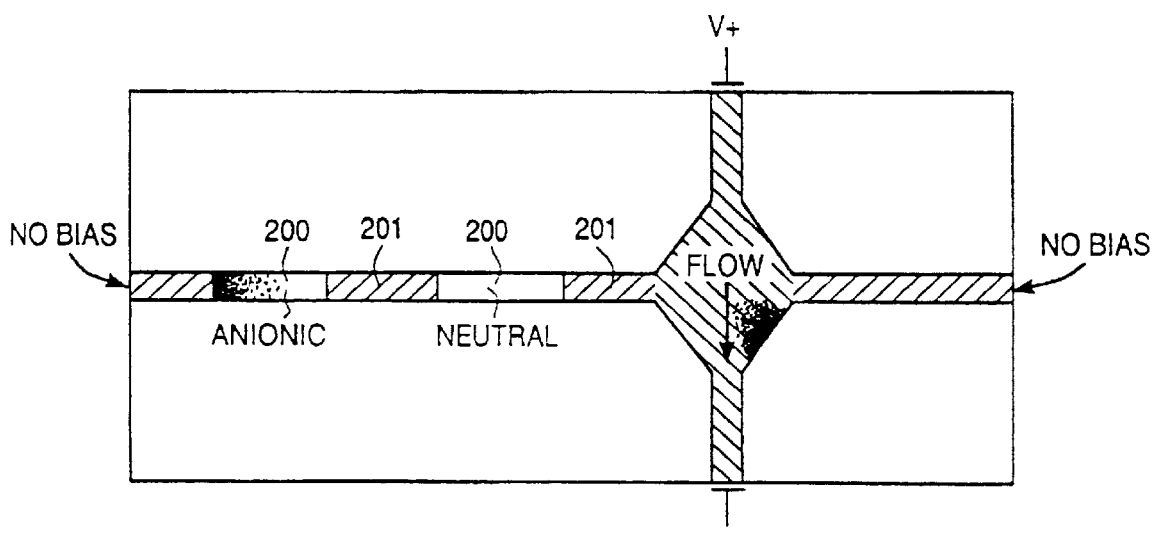

In FIG. 6A a plug 200 of cationic subject material is moving along the channel 152 towards the channel 156. By the time the plug 200 reaches the chamber 160, the subject material has undergone electrophoresis so that the material is more concentrated at the forward end of the subject material region 200. This is illustrated by FIG. 6B. Then the voltage drop impressed along the channels 152 and 156 is terminated and a voltage drop is created along the channels 154 and 150 to draw the subject material region 200 into the channel 150. The sidewalls 162 and 168 of the chamber 160 funnel the subject material region 200 with its electrophoretically biased subject material. This is illustrated by FIG. 6C. By diffusion the subject material is spread across the width of the channel 150 before the subject material travels any significant distance along the channel 150; the subject material in the subject material region 200 is mixed and ready for the next step of operation in the microfluidic system 100.

In addition to its use in correcting electrophoretic bias within a single sample, it will be appreciated that the structure shown in FIG. 6 will be useful in mixing fluid elements within these microfluidic devices, e.g., two distinct subject materials, buffers, reagents, etc.

EXAMPLES

Example 1

Forced Co-migration of Differentially Charged Species, in Electropipettor-type Format In order to demonstrate the efficacy of methods used to eliminate or reduce electrophoretic bias, two oppositely charged species were electrokinetically pumped in a capillary channel, and comigrated in a single sample plug. A Beckman Capillary Electrophoresis system was used to model the electrophoretic forces in a capillary channel.

In brief, a sample containing benzylamine and benzoic acid in either low ionic concentration (or "low salt") (5 mM borate), or high ionic concentration ("high salt") (500 mM borate) buffer, pH 8.6, was used in this experiment. The benzoic acid was present at approximately 2× the concentration of the benzylamine. All injections were timed for 0.17 minutes. Injection plug length was determined by the injection voltage, 8 or 30 kV. The low salt and high salt buffers were as described above.

Figure 7A:
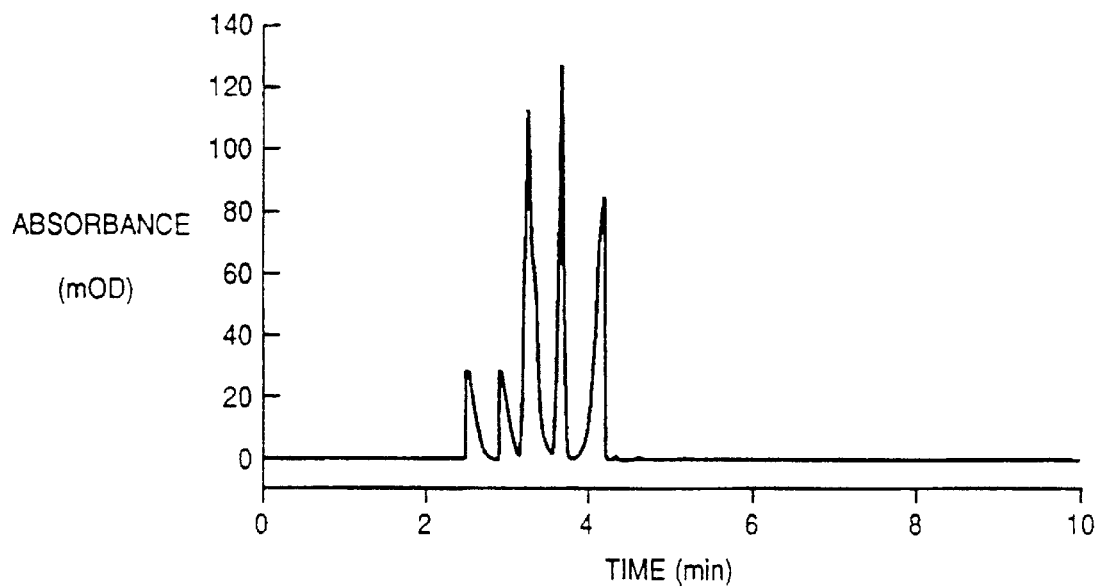
FIG. 7A shows the results of three injections of a sample fluid made up of two oppositely charged chemical species in a low salt buffer, into a capillary filled with low salt buffer.

In a first experiment, three successive injections of sample in low salt buffer were introduced into a capillary filled with low salt buffer. Injections were performed at 8 kV and they were spaced by low salt injections at 30 kV. Data from these injections is shown in FIG. 7A. These data show that benzylamine (identifiable as short peaks, resulting from its lesser concentration) from the first and second injections precede the benzoic acid peak (tall peak) from the first injection. Further, the benzylamine peak from the third injection is nearly coincident with the first benzoic acid peak. Thus, this experiment illustrates the effects of electrophoretic bias, wherein sample peaks may not exit a capillary channel in the same order they entered the channel. As can be clearly seen, such separations can substantially interfere with characterization of a single sample, or worse, compromise previously or subsequently introduced samples.

Figure 7B:
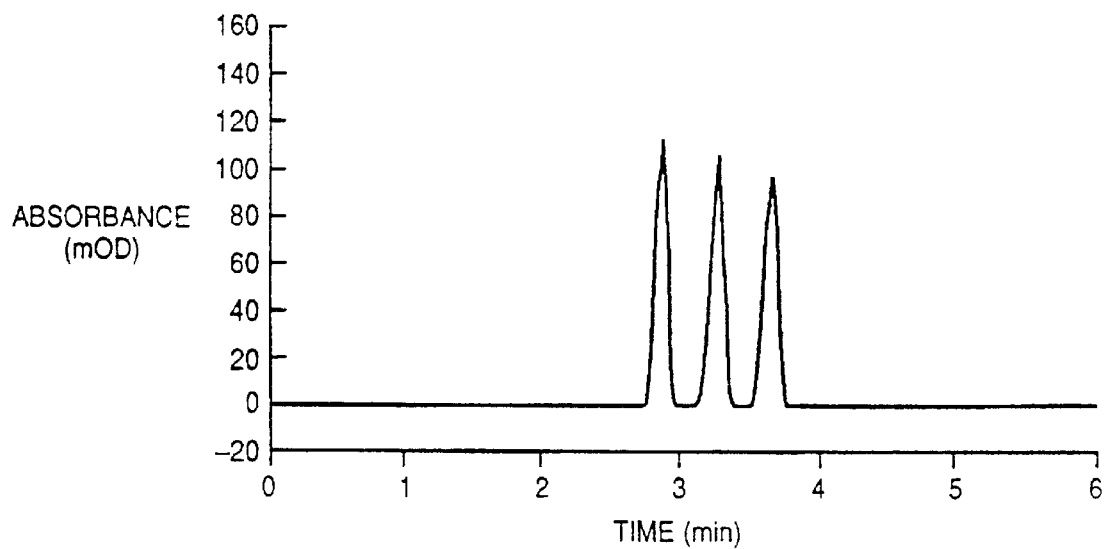
FIG. 7B shows the results of three sample injections where the sample is in high salt buffer, high salt buffer fluids were injected at either end of the sample region to function as guard bands, and the sample/guard bands were run in a low salt buffer filled capillary.

In a second experiment, the capillary was filled with low salt buffer. Samples were injected by first introducing/ injecting high salt buffer into the capillary at 8 kV (first spacer region 1). This was followed by injection of the sample in high salt buffer at 8 kV, which was followed by a second injection of high salt buffer at 8 kV (first spacer region 2). Three samples were injected in this manner, and spaced apart by injecting a low salt buffer at 30 kV. As can be seen in FIG. 7B, both compounds contained in the sample were forced to co-migrate through the capillary channel in the same sample plug, and are represented by a single peak from each injection. This demonstrates sample registration, irrespective of electrophoretic mobility.

Figure 7C:
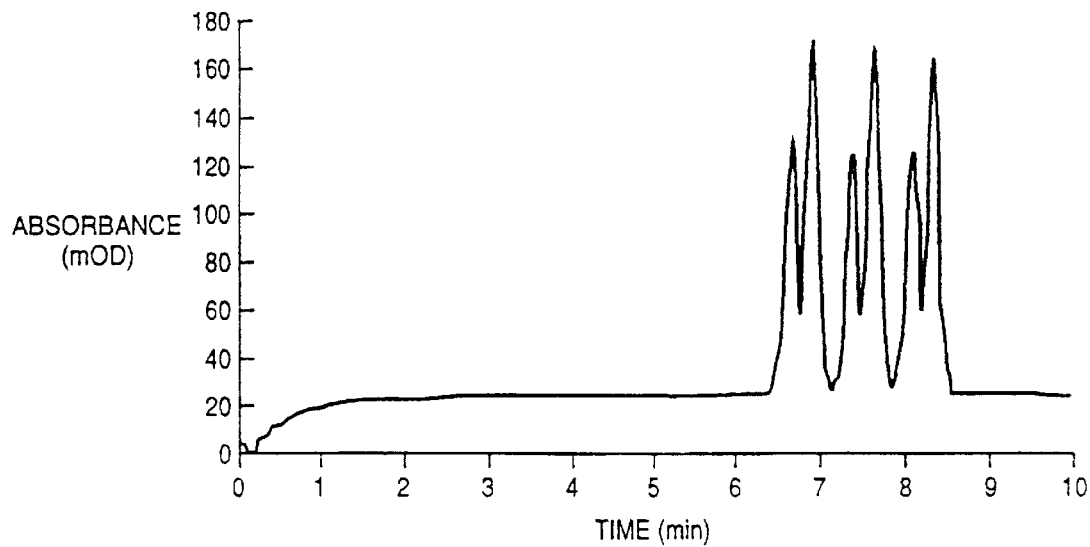
FIG. 7C shows the results of three sample injections similar to that of FIG. 7B except that the size of the low salt spacer region between the sample/high salt spacers (guard bands) is reduced, allowing partial resolution of the species within the sample, without allowing the sample elements to compromise subsequent or previous samples.

By reducing the size of the low salt spacer plug between the samples, relative to the size of the samples, partial resolution of the components of each sample injection can be accomplished. This may be useful where some separation of a sample is desired during electrokinetic pumping, but without compromising subsequently or previously injected samples. This was carried out by injecting the low-salt spacer plug at 8 kV rather than 30 kV. The data from this example is shown in FIG. 7C.

Figure 9C:
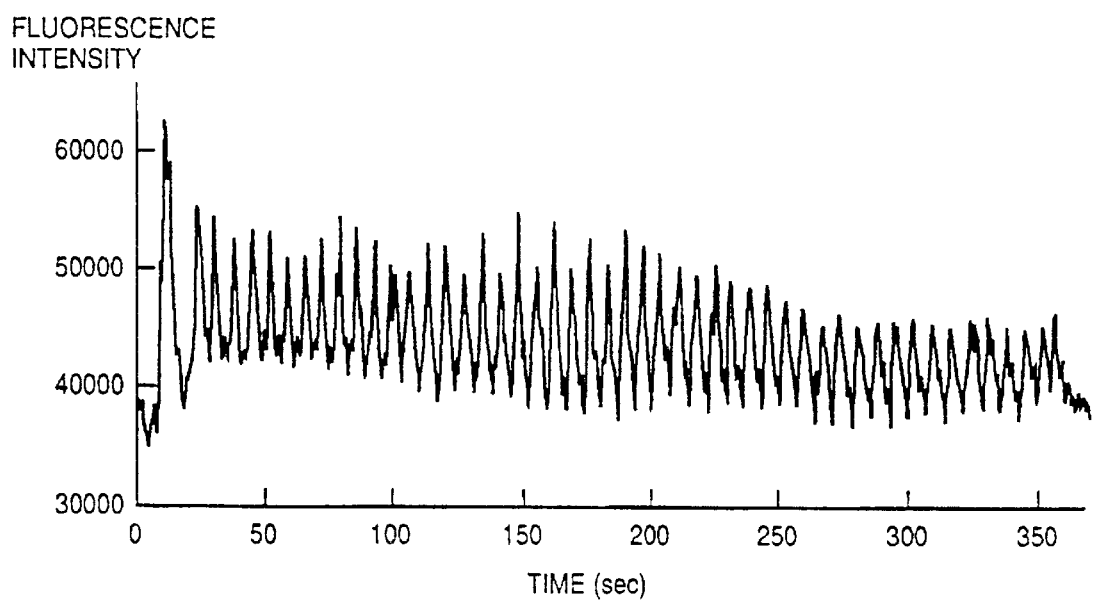
FIG. 9C is a plot which illustrates the movement of the sample fluid and chemical species through an electropipettor formed from an air abraded substrate.
Figure 9A:
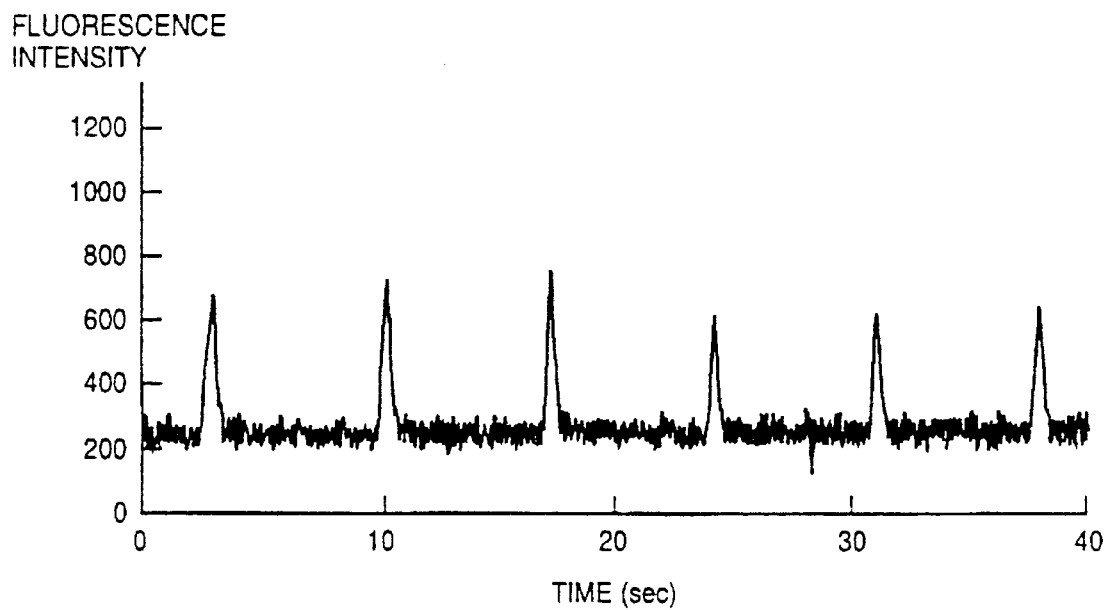
FIG. 9A is a plot of fluorescence versus time which illustrates the movement of a sample fluid made up of test chemical species which is periodically injected into, and moved through, an electropipettor, according to the present invention.
Figure 9B:
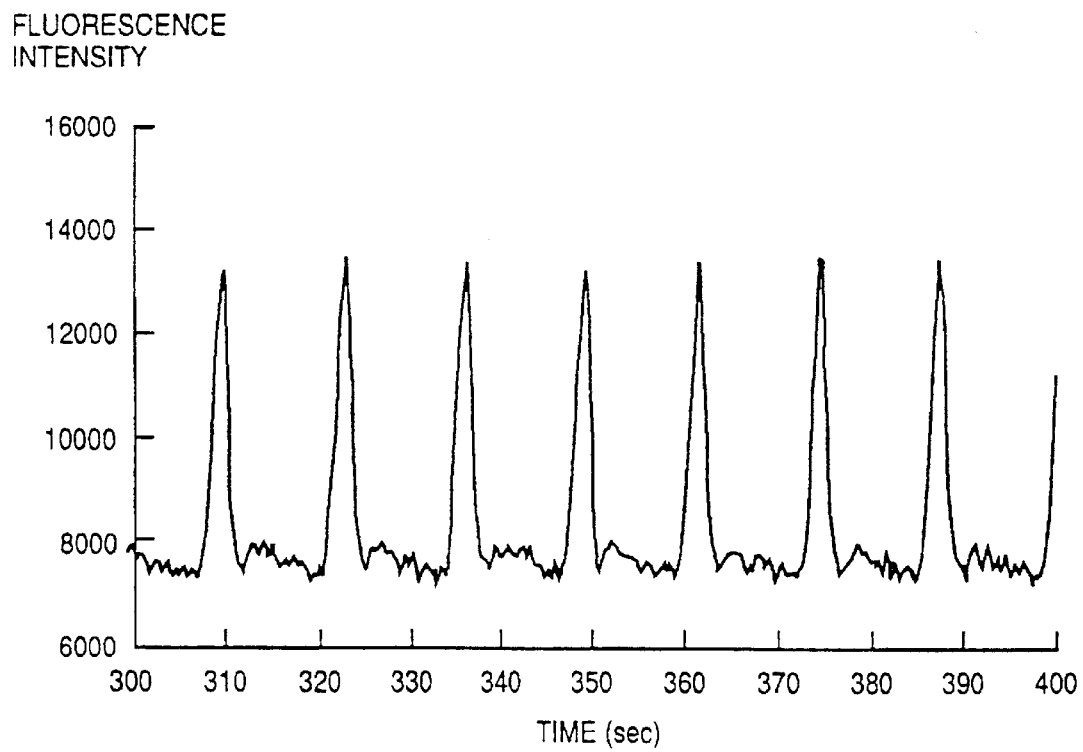
FIG. 9B is another plot which shows the movement of the sample fluid with the chemical species through a microfluidic substrate which is connected to the electropipettor, under different parameters.

Example 2
Migration of Subject Materials through Electropipettor into Microfluidic System Substrate FIGS. 9A–9C illustrate the experimental test results of the introduction of a subject material, i.e., a sample, into a microfluidic system substrate through an electropipettor as described above. The sample is rhodamine B in a phosphate buffered saline solution, pH 7.4. A high ionic concentration ("high salt") buffer was also formed from the phosphate buffered saline solution, pH 7.4. A low ionic concentration ("low salt") buffer was formed from 5 mM Na borate, pH 8.6, solution.

In the tests subject material regions containing the fluorescent rhodamine B were periodically injected into the capillary channel of an electropipettor which is joined to a microfluidic system substrate. High salt and low salt buffers were also injected between the subject material regions, as described previously. FIG. 9A is a plot of the fluorescence intensity of the rhodamine B monitored at a point along the capillary channel near its junction with a channel of the substrate versus time. (In passing, it should be observed that the numbers on fluorescent intensity axis of the FIGS. 9A–9C and 10 plots are for purposes of comparative reference, rather than absolute values.) The injection cycle time was 7 seconds and the electric field to move the subject material regions through the electropipettor was 1000 volts/ cm. The integration time for the photodiode monitoring light from the capillary channel was set at 10 msec. From the FIG. 9A plot, it should be readily evident that light intensity spikes appear at 7 second intervals, matching the injection cycle time of the fluorescent rhodamine B.

In another experiment, the same buffers were used with the rhodamine B samples. The monitoring point was in the channel of the substrate connected to the electropipettor. The injection cycle time was set at 13.1 seconds and the voltage between the source reservoir containing the rhodamine B and destination reservoir in the substrate set at −3000 volts. The monitoring photodiode integration time was 400 msec. As shown in FIG. 9B, the fluorescent intensity spikes closely match the rhodamine B injection cycle time.

The results of a third experimental test asks illustrated in FIG. 9C. In this experiment the electropipettor was formed from a substrate and shaped by air abrasion. The monitoring point is along the capillary channel formed in the substrate (and a planar cover). Here the sample material is 100 μM of rhodamine B in a buffer of PBS, pH 7.4. The high salt buffer solution of PBS, pH 7.4, and a low salt buffer solution of 5 mM Na borate, pH 8.6, are also used. Again periodic spikes of fluorescent intensity match the cyclical injection of rhodamine B into the electropipettor.

Figure 10:
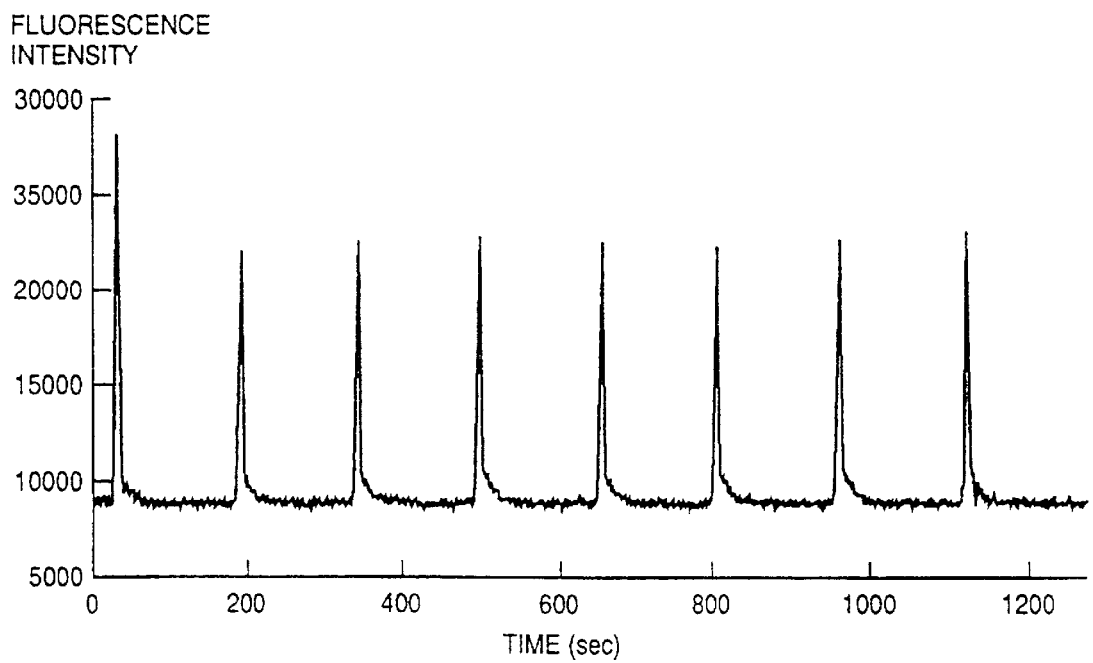
FIG. 10 is a plot which again illustrates the movement of a chemical species in a sample fluid which has been periodically injected into an electropipettor, according to the present invention. In this experiment, the species is a small molecule compound.

FIG. 10 illustrates the results of the cyclical injection of another subject material into an electropipettor, according to the present invention. In this experiment the sample was a small molecule compound of 100 μM with 1% DMSO in a phosphate buffered saline solution, pH 7.4. A high salt buffer of the same phosphate buffered saline solution, pH 7.4, and a low salt buffer of 5 mM Na borate, pH 8.6, was also used. The applied voltage to move the subject material regions through the electropipettor was −4000 volts, and the integration time for the photodiode monitoring light from the capillary channel was set at 400 msec. The samples were periodically injected into the electropipettor as described previously. As in the previous results, the FIG. 10 plot illustrates that for small molecule compounds, the electropipettor moves the samples at evenly spaced time (and space) intervals.

While the foregoing invention has been described in some detail for purposes of clarity and understanding, it will be clear to one skilled in the art from a reading of this disclosure that various changes in form and detail can be made without departing from the true scope of the invention. For example, all the techniques described above may be used in various combinations. All publications and patent documents cited in this application are incorporated by reference in their entirety for all purposes to the same extent as if each individual publication or patent document were so individually denoted.

What is claimed is:

1. A microfluidic device comprising:
   a body having at least first and second intersecting microfluidic channels disposed therein wherein the first and second microfluidic channels comprise different depths;
   a pipettor for sampling a plurality of different sample materials, the pipettor having a first capillary channel disposed therein, the first capillary channel being fluidly connected at a first end to the first microfluidic channel, whereby materials flowed through the capillary channel flow into the first channel.

2. The method of claim 1, wherein the first microfluidic channel is two times deeper than the second microfluidic channel.

3. The microfluidic device of claim 1, wherein the first microfluidic channel is at least five times deeper than the second microfluidic channel.

4. The microfluidic device of claim 1, wherein the pipettor comprises a capillary tube.

5. The microfluidic device of claim 1, wherein the body comprises:
   a first planar substrate having a first surface, the first and second intersecting channels being fabricated on the first surface; and
   a second planar substrate overlaying the first surface of the first substrate, fluidly sealing the first and second channels to define conduits.

6. The microfluidic device of claim 5, wherein at least one of the first and second substrates comprises at least first and second apertures disposed therethrough, the first and second apertures being fluidly connected to the first and second channels, respectively, when the second substrate is overlaid on the first substrate.

7. The microfluidic device of claim 5, wherein the pipettor is formed from at least one of the first and second substrates.

8. The microfluidic device of claim 5, wherein at least one of the first and second substrates comprises glass.

9. The microfluidic device of claim 5, wherein at least one of the first and second substrates comprises a polymeric material.

10. The microfluidic device of claim 1, wherein the capillary channel comprises a cross-sectional dimension of between about 1 and about 100 μm.

11. The microfluidic device of claim 1, wherein the first capillary channel is open at a second end.

12. The microfluidic device of claim 1, further comprising a multi-well plate having a plurality of sample materials disposed therein, the multi-well plate being positioned adjacent the first end of the capillary channel.

13. The microfluidic device of claim 1, further comprising a sample matrix having a plurality of sample materials immobilized thereon, the sample matrix being positioned adjacent the first end of the capillary channel.

14. The microfluidic device of claim 13, wherein the plurality of sample materials are dried onto the sample matrix.

15. The microfluidic device of claim 13, wherein the sample matrix comprises a porous matrix.

16. The microfluidic device of claim 13, wherein the sample matrix comprises a charged matrix.

17. The microfluidic device of claim 13, wherein the sample matrix comprises a hydrophobic matrix.

18. The microfluidic device of claim 13, wherein the sample matrix comprises a hydrophilic matrix.

19. The microfluidic device of claim 13, wherein the sample matrix comprises hydrophilic regions surrounded by hydrophobic barriers, the sample materials being disposed in the hydrophilic regions.

20. The microfluidic device of claim 13, wherein the sample matrix comprises hydrophobic regions surrounded by hydrophilic barriers, the sample materials being disposed in the hydrophobic regions.

21. The microfluidic device of claim 13, wherein the sample matrix comprises a membrane selected from cellulose, nitrocellulose, PVDF, nylon and polysulfone.

22. The microfluidic device of claim 13, wherein the sample matrix comprises at least a thousand different sample materials.

23. The microfluidic device of claim 13, wherein the sample matrix comprises at least one hundred thousand different sample materials.

24. The microfluidic device of claim 13, further comprising a fluid direction system operably coupled to the pipettor for expelling a quantity of solubilizing liquid from the pipettor onto the sample matrix to solubilize a sample material immobilized thereon, and for drawing the solubilized sample material into the pipettor.

25. The microfluidic device of claim 13, further comprising a translation system for moving the sample matrix relative to the pipettor.

26. The microfluidic device of claim 13, wherein the second end of the first capillary channel is configured to retain a volume of expelled solubilizing fluid thereon.

27. The microfluidic device of claim 26, wherein the first end of the capillary channel is open in a sample cup at an end of the pipettor, the sample cup being configured to retain a volume of solubilizing fluid therein.

28. A method of sampling subject materials, comprising:
providing a microfluidic device which comprises:
a body having at least first and second intersecting microfluidic channels disposed therein;
a pipettor for sampling a plurality of different fluids, the pipettor having a capillary channel disposed therein, the capillary channel having first and second ends being fluidly connected at the second end to the first microfluidic channel, whereby materials flowed through the capillary channel flow into the first channel;
contacting the first end of the capillary channel with a source of a first test compound;
drawing a first test compound into the capillary channel; and transporting the first test compound from the capillary channel into the first microfluidic channel;
contacting the first end of the capillary channel with a source of spacer material; and
drawing the spacer material into the capillary channel, after said step of drawing said first test compound into said capillary channel.

29. The method of claim 28, wherein the first test compound comprises DMSO.

30. The method of claim 28, wherein the microfluidic channel system is disposed in a first substrate and the providing step comprises providing the capillary tube attached at one end to the first substrate.

31. The method of claim 28, wherein the step of drawing the first test compound into the capillary channel comprises electrokinetically moving the first test compound into the capillary channel.

32. The method of claim 28, wherein the step of drawing the first test compound into the capillary channel comprises electroosmotically drawing the first test compound into the capillary channel.

33. The method of claim 28, wherein the step of transporting the first test compound from the capillary channel into the first microfluidic channel comprises electrokinetically transporting the first test compound from the capillary channel to the first microfluidic channel.

34. The method of claim 33, wherein the step of electrokinetically transporting the first test compound from the capillary channel into the first microfluidic channel comprises providing a voltage drop between the second end of the capillary channel and a reservoir connected to the first microfluidic channel.

35. The method of claim 33, wherein the step of electrokinetically transporting the first test compound from the capillary channel into the first microfluidic channel comprises electroosmotically transporting the sample material into the first microfluidic channel.

36. A method of sampling subject materials, comprising:
providing a microfluidic device which comprises:
a body having at least first and second intersecting microfluidic channels disposed therein;
a pipettor for sampling a plurality of different fluids, the pipettor having a capillary channel disposed therein, the capillary channel having first and second ends being fluidly connected at the second end to the first microfluidic channel, whereby materials flowed through the capillary channel flow into the first channel;
contacting the first end of the capillary channel with a source of a first test compound;
drawing a first test compound into the capillary channel; and transporting the first test compound from the capillary channel into the first microfluidic channel;

contacting the first end of the capillary channel with a source of a second test compound;

drawing at least a second test compound into the capillary channel; and transporting the second test compound from the capillary channel into the first microfluidic channel.

37. The method of claim 36, wherein the first test compound comprises DMSO.

38. The method of claim 36, wherein the microfluidic channel system is disposed in a first substrate and the providing step comprises providing the capillary tube attached at one end to the first substrate.

39. The method of claim 36, wherein the step of drawing the first test compound into the capillary channel comprises electrokinetically moving the first test compound into the capillary channel.

40. The method of claim 36, wherein the step of drawing the first test compound into the capillary channel comprises electroosmotically drawing the first test compound into the capillary channel.

41. The method of claim 36, wherein the step of transporting the first test compound from the capillary channel into the first microfluidic channel comprises electrokinetically transporting the first test compound from the capillary channel to the first microfluidic channel.

42. The method of claim 41, wherein the step of electrokinetically transporting the first test compound from the capillary channel into the first microfluidic channel comprises providing a voltage drop between the second end of the capillary channel and a reservoir connected to the first microfluidic channel.

43. The method of claim 41, wherein the step of electrokinetically transporting the first test compound from the capillary channel into the first microfluidic channel comprises electroosmotically transporting the sample material into the first microfluidic channel.

44. A method of introducing a sample material into a microfluidic channel system, comprising:

introducing the sample material into a capillary channel in a capillary tube;

providing the capillary channel having first and second ends in fluid communication at the first end with at least one microscale channel of the microfluidic channel system;

moving the sample material from the capillary channel into the at least one microscale channel;

wherein the sample material is bounded by at least a first spacer material region.

45. The method of claim 44, wherein the sample material is bounded by at least first and second spacer material regions.

46. The method of claim 44, wherein the first test compound comprises DMSO.

47. The method of claim 44, wherein the microfluidic channel system is disposed in a first substrate and the providing step comprises providing the capillary tube attached at one end to the first substrate.

48. The method of claim 44, wherein the step of drawing the first test compound into the capillary channel comprises electrokinetically moving the first test compound into the capillary channel.

49. The method of claim 44, wherein the step of drawing the first test compound into the capillary channel comprises electroosmotically drawing the first test compound into the capillary channel.

50. The method of claim 44, wherein the step of transporting the first test compound from the capillary channel into the first microfluidic channel comprises electrokinetically transporting the first test compound from the capillary channel to the first microfluidic channel.

51. The method of claim 50, wherein the step of electrokinetically transporting the first test compound from the capillary channel into the first microfluidic channel comprises providing a voltage drop between the second end of the capillary channel and a reservoir connected to the first microfluidic channel.

52. The method of claim 50, wherein the step of electrokinetically transporting the first test compound from the capillary channel into the first microfluidic channel comprises electroosmotically transporting the sample material into the first microfluidic channel.

53. A microfluidic device comprising:

a body having at least first and second intersecting microfluidic channels disposed therein;

a pipettor for sampling a plurality of different fluids, the pipettor having a first capillary channel disposed therein, the first capillary channel being fluidly connected at a first end to the first microfluidic channel, whereby materials flowed through the capillary channel flow into the first channel, and wherein the first capillary channel is open at a second end, wherein the pipettor further comprises a second capillary channel, the second capillary channel being in fluid communication with a source of solubilizing liquid at a first end and being open at a second end adjacent the second end of the first capillary channel.

54. A microfluidic device comprising:

a body having at least first and second intersecting microfluidic channels disposed therein;

a pipettor for sampling a plurality of different fluids, the pipettor having a first capillary channel disposed therein, the first capillary channel being fluidly connected at a first end to the first microfluidic channel, whereby materials flowed through the capillary channel flow into the first channel, and wherein the first capillary channel is open at a second end; and a sample matrix having a plurality of sample materials immobilized thereon, the sample matrix being positioned adjacent the second end of the capillary channel.

55. The microfluidic device of claim 54, wherein the plurality of sample materials are dried onto the sample matrix.

56. The microfluidic device of claim 54, wherein the sample matrix comprises a porous matrix.

57. The microfluidic device of claim 54, wherein the sample matrix comprises a charged matrix.

58. The microfluidic device of claim 54, wherein the sample matrix comprises a hydrophobic matrix.

59. The microfluidic device of claim 54, wherein the sample matrix comprises a hydrophilic matrix.

60. The microfluidic device of claim 54, wherein the sample matrix comprises hydrophilic regions surrounded by hydrophobic barriers, the sample materials being disposed in the hydrophilic regions.

61. The microfluidic device of claim 54, wherein the sample matrix comprises hydrophobic regions surrounded by hydrophilic barriers, the sample materials being disposed in the hydrophobic regions.

62. The microfluidic device of claim 54, wherein the sample matrix comprises a membrane selected from cellulose, nitrocellulose, PVDF, nylon and polysulfone.

63. The microfluidic device of claim 54, wherein the sample matrix comprises at least a thousand different sample materials.

64. The microfluidic device of claim 54, wherein the sample matrix comprises at least one hundred thousand different sample materials.

65. The microfluidic device of claim 54, further comprising a fluid direction system operably coupled to the pipettor for expelling a quantity of solubilizing liquid from the pipettor onto the sample matrix to solubilize a sample material immobilized thereon, and for drawing the solubilized sample material into the pipettor.

66. The microfluidic device of claim 54, further comprising a translation system for moving the sample matrix relative to the pipettor.

67. The microfluidic device of claim 54, wherein the second end of the first capillary channel is configured to retain a volume of expelled solubilizing fluid thereon.

68. The microfluidic device of claim 67, wherein the second end of the capillary channel is open in a sample cup at an end of the pipettor, the sample cup being configured to retain a volume of solubilizing fluid therein.

69. The microfluidic device of claim 54, wherein the pipettor comprises a capillary tube.

70. The microfluidic device of claim 54, wherein the body comprises:
a first planar substrate having a first surface, the first and second intersecting channels being fabricated on the first surface; and
a second planar substrate overlaying the first surface of the first substrate, fluidly sealing the first and second channels to define conduits.

71. The microfluidic device of claim 70, wherein at least one of the first and second substrates comprises at least first and second apertures disposed therethrough, the first and second apertures being fluidly connected to the first and second channels, respectively, when the second substrate is overlaid on the first substrate.

72. The microfluidic device of claim 70, wherein the pipettor is formed from at least one of the first and second substrates.

73. The microfluidic device of claim 70, wherein at least one of the first and second substrates comprises glass.

74. The microfluidic device of claim 70, wherein at least one of the first and second substrates comprises a polymeric material.

75. The microfluidic device of claim 54, wherein the capillary channel comprises a cross-sectional dimension of between about 1 and about 100 µm.

76. A method of sampling subject materials, comprising:
providing a microfluidic device which comprises:
a body having at least first and second intersecting microfluidic channels disposed therein;
a pipettor for sampling a plurality of different fluids, the pipettor having a capillary channel disposed therein, the capillary channel having first and second ends being fluidly connected at the second end to the first microfluidic channel, whereby materials flowed through the capillary channel flow into the first channel;
contacting the first end of the capillary channel with a source of a first test compound;
drawing a first test compound into the capillary channel; and
transporting the first test compound from the capillary channel into the first microscale channel, wherein the source of first test compounds in the contacting step comprises a sample matrix having a plurality of samples immobilized thereon.

77. The method of claim 76, wherein in the contacting step the sample matrix comprises a plurality of different samples spotted onto the sample matrix in fixed positions.

78. The method of claim 76, wherein the contacting step comprises solubilizing the sample material on the sample matrix, the solubilized sample being drawn into the capillary channel during thy drawing step.

79. The method of claim 78, wherein the step of solubilizing the sample material is carried out using a quantity of solubilizing fluid present at the first end of the capillary channel.

80. The method of claim 79, wherein the solubilizing step comprises expelling a quantity of solubilizing fluid from the first end of the capillary onto the sample matrix to solubilize the sample material on the sample matrix.

81. The method of claim 76, wherein the solubilizig step comprises expelling a quantity of solubilizing fluid from an end of a second channel, the second channel end being adjacent to the first end of the capillary channel.

82. The method of claim 76, further comprising translating the sample matrix relative to the pipettor, and repeating the contacting, drawing and transporting steps with a second test compound.

83. The method of claim 76, further comprising repeating the translating, contacting, drawing a transporting steps with at least 1000 different test compounds immobilized on the sample matrix.

84. The method of claim 76, further comprising repeating the translating, contacting, drawing a transporting steps with at least 100,000 different test compounds immobilized on a sample matrix.

85. The method of claim 76, wherein the first test compound comprises DMSO.

86. The method of claim 76, wherein the microfluidic channel system is disposed in a first substrate and the providing step comprises providing the capillary tube attached at one end to the first substrate.

87. The method of claim 76, wherein the step of drawing the first test compound into the capillary channel comprises electrokinetically moving the first test compound into the capillary channel.

88. The method of claim 76, wherein the step of drawing the first test compound into the capillary channel comprises electroosmotically drawing the first test compound into the capillary channel.

89. The method of claim 76, wherein the step of transporting the first test compound from the capillary channel into the first microfluidic channel comprises electrokinetically transporting the first test compound from the capillary channel to the first microfluidic channel.

90. The method of claim 89, wherein the step of electrokinetically transporting the first test compound from the capillary channel into the first microfluidic channel comprises providing a voltage drop between the second end of the capillary channel and a reservoir connected to the first microfluidic channel.

91. The method of claim 90, wherein the step of electrokinetically transporting the first test compound from the capillary channel into the first microfluidic channel comprises electroosmotically transporting the sample material into the first microfluidic channel.

* * * * *

UNITED STATES PATENT AND TRADEMARK OFFICE
CERTIFICATE OF CORRECTION

PATENT NO. : 6,042,709
DATED : March 28, 2000
INVENTOR(S) : J. Wallace Parce, et. al.

It is certified that error appears in the above-identified patent and that said Letters Patent is hereby corrected as shown below:

Claim 2, at line 1, please delete "method" and insert --microfluidic device--.

Claim 78, at line 4, please delete "thy" and insert --the--.

Claim 81, at line 1, please delete "solubilizig" and insert --solubilizing--.

Claim 83, at line 2, please delete "a" and insert --and--.

Claim 84, at line 2, please delete "a" and insert --and--.

Signed and Sealed this

Twenty-seventh Day of February, 2001

*Attest:*

NICHOLAS P. GODICI

*Attesting Officer*     *Acting Director of the United States Patent and Trademark Office*